United States Patent
Hartwell et al.

(10) Patent No.: US 11,097,044 B2
(45) Date of Patent: Aug. 24, 2021

(54) COMPRESSIBLE WOUND FILLERS AND SYSTEMS AND METHODS OF USE IN TREATING WOUNDS WITH NEGATIVE PRESSURE

(71) Applicant: Smith & Nephew PLC, Watford (GB)

(72) Inventors: Edward Yerbury Hartwell, Hull (GB); John Kenneth Hicks, Pocklington (GB); Carl Saxby, Brough (GB); Elizabeth Mary Huddleston, Copmanthorpe (GB); John Christian Hoggarth, York (GB); Tim Stern, Belper (GB); Andrew Linton, Yorkshire (GB)

(73) Assignee: Smith & Nephew PLC, Watford (GB)

( * ) Notice: Subject to any disclaimer, the term of this patent is extended or adjusted under 35 U.S.C. 154(b) by 235 days.

(21) Appl. No.: 16/221,313

(22) Filed: Dec. 14, 2018

(65) Prior Publication Data

US 2019/0231945 A1    Aug. 1, 2019

Related U.S. Application Data

(63) Continuation of application No. 14/774,695, filed as application No. PCT/GB2014/050746 on Mar. 13, 2014, now Pat. No. 10,159,771.

(Continued)

(51) Int. Cl.
*A61M 1/00* (2006.01)
*A61F 13/00* (2006.01)
*A61F 13/02* (2006.01)

(52) U.S. Cl.
CPC ......... *A61M 1/90* (2021.05); *A61F 13/00068* (2013.01); *A61F 13/0216* (2013.01); *A61M 2210/1021* (2013.01)

(58) Field of Classification Search
CPC .. A61M 1/0088; A61M 1/009; A61M 1/0092; A61M 2210/1021; A61M 1/90;

(Continued)

(56) References Cited

U.S. PATENT DOCUMENTS 3,014,483 A    12/1961    Frank et al.
3,194,239 A    7/1965    Sullivan (Continued)

FOREIGN PATENT DOCUMENTS

AU    2012261793 B2    11/2014
AU    2013206230 B2    5/2016

(Continued)

OTHER PUBLICATIONS

"Definition of 3D Printer," American Heritage Dictionary of the English Language, Fifth Edition, accessed on Feb. 22, 2018 from URL: https://www.thefreedictionary.co, 2016, 1 page.

(Continued)

*Primary Examiner* — Philip R Wiest
(74) *Attorney, Agent, or Firm* — Knobbe, Martens, Olson & Bear, LLP

(57) ABSTRACT

Apparatuses and methods disclosed herein relate to various embodiments of wound fillers that, in some cases, preferentially collapse in one direction as compared to another direction. Such apparatuses and methods may aid in the closure of wounds and may further be used in combination with pressure sensors and controllers to provide for controlled collapse of the wound fillers.

9 Claims, 12 Drawing Sheets

Related U.S. Application Data

(60) Provisional application No. 61/784,868, filed on Mar. 14, 2013.

(58) Field of Classification Search
CPC ............ A61F 13/00068; A61F 13/0216; A61F 13/00021; A61F 13/00025; A61F 13/00051; A61F 13/00038
See application file for complete search history.

(56) References Cited

U.S. PATENT DOCUMENTS

| | | | |
|---|---|---|---|
| 3,578,003 A | 5/1971 | Everett |
| 3,789,851 A | 2/1974 | Leveen |
| 3,812,616 A | 5/1974 | Koziol |
| 4,467,805 A | 8/1984 | Fukuda |
| 4,608,041 A | 8/1986 | Nielsen |
| 4,637,819 A | 1/1987 | Ouellette et al. |
| 4,699,134 A | 10/1987 | Samuelsen |
| 4,815,468 A | 3/1989 | Annand |
| 5,176,663 A | 1/1993 | Svedman et al. |
| 5,264,218 A | 11/1993 | Rogozinski |
| 5,368,910 A | 11/1994 | Langdon |
| 5,376,067 A | 12/1994 | Daneshvar |
| 5,409,472 A | 4/1995 | Rawlings et al. |
| 5,415,715 A | 5/1995 | Delage et al. |
| 5,423,857 A | 6/1995 | Rosenman et al. |
| 5,512,041 A | 4/1996 | Bogart |
| 5,514,105 A | 5/1996 | Goodman, Jr. et al. |
| 5,562,107 A | 10/1996 | Lavender et al. |
| 5,584,859 A | 12/1996 | Brotz |
| 5,636,643 A | 6/1997 | Argenta et al. |
| 5,695,777 A | 12/1997 | Donovan et al. |
| 5,928,210 A | 7/1999 | Ouellette et al. |
| 5,960,497 A | 10/1999 | Castellino et al. |
| 6,080,168 A | 6/2000 | Levin et al. |
| 6,086,591 A | 7/2000 | Bojarski |
| 6,142,982 A | 11/2000 | Hunt et al. |
| 6,176,868 B1 | 1/2001 | Detour |
| 6,291,050 B1 | 9/2001 | Cree et al. |
| 6,503,208 B1 | 1/2003 | Skovlund |
| 6,530,941 B1 | 3/2003 | Muller et al. |
| 6,548,727 B1 | 4/2003 | Swenson |
| 6,553,998 B2 | 4/2003 | Heaton et al. |
| 6,566,575 B1 | 5/2003 | Stickels et al. |
| 6,685,681 B2 | 2/2004 | Lockwood et al. |
| 6,695,823 B1 | 2/2004 | Lina et al. |
| 6,712,830 B2 | 3/2004 | Esplin |
| 6,712,839 B1 | 3/2004 | Lonne |
| 6,767,334 B1 | 7/2004 | Randolph |
| 6,770,794 B2 | 8/2004 | Fleischmann |
| 6,787,682 B2 | 9/2004 | Gilman |
| 6,814,079 B2 | 11/2004 | Heaton et al. |
| 6,883,531 B1 | 4/2005 | Perttu |
| 6,893,452 B2 | 5/2005 | Jacobs |
| 6,936,037 B2 | 8/2005 | Bubb et al. |
| 6,951,553 B2 | 10/2005 | Bubb et al. |
| 6,977,323 B1 | 12/2005 | Swenson |
| 6,994,702 B1 | 2/2006 | Johnson |
| 7,004,915 B2 | 2/2006 | Boynton et al. |
| 7,025,755 B2 | 4/2006 | Epstein et al. |
| 7,070,584 B2 | 7/2006 | Johnson et al. |
| 7,117,869 B2 | 10/2006 | Heaton et al. |
| 7,128,735 B2 | 10/2006 | Weston et al. |
| 7,144,390 B1 | 12/2006 | Hannigan et al. |
| 7,153,312 B1 | 12/2006 | Torrie et al. |
| 7,156,862 B2 | 1/2007 | Jacobs et al. |
| 7,172,615 B2 | 2/2007 | Morriss et al. |
| 7,189,238 B2 | 3/2007 | Lombardo et al. |
| 7,196,054 B1 | 3/2007 | Drohan et al. |
| 7,198,046 B1 | 4/2007 | Argenta et al. |
| 7,216,651 B2 | 5/2007 | Argenta et al. |
| D544,092 S | 6/2007 | Lewis |
| 7,262,174 B2 | 8/2007 | Jiang et al. |
| 7,279,612 B1 | 10/2007 | Heaton et al. |
| 7,315,183 B2 | 1/2008 | Hinterscher |
| 7,351,250 B2 | 4/2008 | Zamierowski |
| 7,361,184 B2 | 4/2008 | Joshi |
| 7,367,342 B2 | 5/2008 | Butler |
| 7,381,211 B2 | 6/2008 | Zamierowski |
| 7,381,859 B2 | 6/2008 | Hunt et al. |
| 7,413,571 B2 | 8/2008 | Zamierowski |
| 7,438,705 B2 | 10/2008 | Karpowicz et al. |
| 7,494,482 B2 | 2/2009 | Orgill et al. |
| 7,534,240 B1 | 5/2009 | Johnson |
| 7,540,848 B2 | 6/2009 | Hannigan et al. |
| 7,553,306 B1 | 6/2009 | Hunt et al. |
| 7,553,923 B2 | 6/2009 | Williams et al. |
| 7,569,742 B2 | 8/2009 | Haggstrom et al. |
| 7,578,532 B2 | 8/2009 | Schiebler |
| D602,583 S | 10/2009 | Pidgeon et al. |
| 7,611,500 B1 | 11/2009 | Lina et al. |
| 7,615,036 B2 | 11/2009 | Joshi et al. |
| 7,617,762 B1 | 11/2009 | Ragner |
| 7,618,382 B2 | 11/2009 | Vogel et al. |
| 7,622,629 B2 | 11/2009 | Aali |
| 7,625,362 B2 | 12/2009 | Boehringer et al. |
| 7,645,269 B2 | 1/2010 | Zamierowski |
| 7,651,484 B2 | 1/2010 | Heaton et al. |
| 7,670,323 B2 | 3/2010 | Hunt et al. |
| 7,678,102 B1 | 3/2010 | Heaton |
| 7,683,667 B2 | 3/2010 | Kim et al. |
| 7,699,823 B2 | 4/2010 | Haggstrom et al. |
| 7,699,830 B2 | 4/2010 | Martin et al. |
| 7,699,831 B2 | 4/2010 | Bengtson et al. |
| 7,700,819 B2 | 4/2010 | Ambrosio et al. |
| 7,708,724 B2 | 5/2010 | Weston et al. |
| 7,713,743 B2 | 5/2010 | Villanueva et al. |
| 7,722,528 B2 | 5/2010 | Arnal et al. |
| 7,723,560 B2 | 5/2010 | Lockwood et al. |
| 7,754,937 B2 | 7/2010 | Boehringer et al. |
| 7,776,028 B2 | 8/2010 | Miller et al. |
| 7,777,522 B2 | 8/2010 | Yang et al. |
| 7,779,625 B2 | 8/2010 | Joshi et al. |
| D625,801 S | 10/2010 | Pidgeon et al. |
| 7,815,616 B2 | 10/2010 | Boehringer et al. |
| 7,820,453 B2 | 10/2010 | Heylen et al. |
| 7,846,141 B2 | 12/2010 | Weston |
| 7,857,806 B2 | 12/2010 | Karpowicz et al. |
| 7,863,495 B2 | 1/2011 | Aali |
| 7,892,181 B2 | 2/2011 | Christensen et al. |
| 7,896,856 B2 | 3/2011 | Petrosenko et al. |
| 7,909,805 B2 | 3/2011 | Weston et al. |
| 7,910,789 B2 | 3/2011 | Sinyagin |
| 7,931,774 B2 | 4/2011 | Hall et al. |
| 7,942,866 B2 | 5/2011 | Radl et al. |
| 7,951,124 B2 | 5/2011 | Boehringer et al. |
| 7,964,766 B2 | 6/2011 | Blott et al. |
| 7,976,519 B2 | 7/2011 | Bubb et al. |
| 7,976,524 B2 | 7/2011 | Kudo et al. |
| 7,981,098 B2 | 7/2011 | Boehringer et al. |
| 8,030,534 B2 | 10/2011 | Radl et al. |
| 8,057,447 B2 | 11/2011 | Olson et al. |
| 8,062,272 B2 | 11/2011 | Weston et al. |
| 8,062,295 B2 | 11/2011 | McDevitt et al. |
| 8,062,331 B2 | 11/2011 | Zamierowski |
| 8,067,662 B2 | 11/2011 | Aali et al. |
| 8,070,773 B2 | 12/2011 | Zamierowski |
| 8,080,702 B2 | 12/2011 | Blott et al. |
| 8,100,887 B2 | 1/2012 | Weston et al. |
| 8,114,126 B2 | 2/2012 | Heaton et al. |
| 8,123,781 B2 | 2/2012 | Zamierowski |
| 8,128,615 B2 | 3/2012 | Martin et al. |
| 8,129,580 B2 | 3/2012 | Wilkes et al. |
| 8,142,419 B2 | 3/2012 | Heaton et al. |
| 8,162,909 B2 | 4/2012 | Blott et al. |
| 8,172,816 B2 | 5/2012 | Kazala, Jr. et al. |
| 8,182,413 B2 | 5/2012 | Browning |
| 8,187,237 B2 | 5/2012 | Seegert |
| 8,188,331 B2 | 5/2012 | Barta et al. |
| 8,197,467 B2 | 6/2012 | Heaton et al. |
| 8,207,392 B2 | 6/2012 | Haggstrom et al. |
| 8,235,955 B2 | 8/2012 | Blott et al. |
| 8,246,606 B2 | 8/2012 | Stevenson et al. |

(56) References Cited

U.S. PATENT DOCUMENTS

| | | |
|---|---|---|
| 8,257,328 B2 | 9/2012 | Augustine et al. |
| 8,273,105 B2 | 9/2012 | Cohen et al. |
| 8,328,776 B2 | 12/2012 | Kelch et al. |
| 8,337,411 B2 | 12/2012 | Nishtala et al. |
| 8,353,931 B2 | 1/2013 | Stopek et al. |
| 8,357,131 B2 | 1/2013 | Olson |
| 8,362,315 B2 | 1/2013 | Aali |
| 8,399,730 B2 | 3/2013 | Kazala, Jr. et al. |
| 8,430,867 B2 | 4/2013 | Robinson et al. |
| 8,444,392 B2 | 5/2013 | Turner et al. |
| 8,447,375 B2 | 5/2013 | Shuler |
| 8,454,990 B2 | 6/2013 | Canada et al. |
| 8,460,257 B2 | 6/2013 | Locke et al. |
| 8,481,804 B2 | 7/2013 | Timothy |
| 8,486,032 B2 | 7/2013 | Seegert et al. |
| 8,500,704 B2 | 8/2013 | Boehringer et al. |
| 8,500,776 B2 | 8/2013 | Ebner |
| 8,523,832 B2 | 9/2013 | Seegert |
| 8,535,296 B2 | 9/2013 | Blott et al. |
| 8,562,576 B2 | 10/2013 | Hu et al. |
| 8,608,776 B2 | 12/2013 | Coward et al. |
| 8,622,981 B2 | 1/2014 | Hartwell et al. |
| 8,632,523 B2 | 1/2014 | Eriksson et al. |
| 8,673,992 B2 | 3/2014 | Eckstein et al. |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,721,629 B2 | 5/2014 | Hardman et al. |
| 8,746,662 B2 | 6/2014 | Poppe |
| 8,747,375 B2 | 6/2014 | Barta et al. |
| 8,764,732 B2 | 7/2014 | Hartwell |
| 8,784,392 B2 | 7/2014 | Vess et al. |
| 8,791,315 B2 | 7/2014 | Lattimore et al. |
| 8,791,316 B2 | 7/2014 | Greener |
| 8,802,916 B2 | 8/2014 | Griffey et al. |
| 8,814,842 B2 | 8/2014 | Coulthard et al. |
| 8,821,535 B2 | 9/2014 | Greener |
| 8,843,327 B2 | 9/2014 | Vernon-Harcourt et al. |
| 8,882,730 B2 | 11/2014 | Zimnitsky et al. |
| 8,936,618 B2 | 1/2015 | Sealy et al. |
| 8,945,030 B2 | 2/2015 | Weston et al. |
| 8,951,235 B2 | 2/2015 | Allen et al. |
| 9,044,579 B2 | 6/2015 | Blott et al. |
| 9,061,095 B2 | 6/2015 | Adie et al. |
| 9,220,822 B2 | 12/2015 | Hartwell |
| 9,302,034 B2 | 4/2016 | Corley |
| 9,408,755 B2 | 8/2016 | Larsson et al. |
| 9,655,807 B2 | 5/2017 | Locke et al. |
| 9,737,649 B2 | 8/2017 | Begin et al. |
| 9,849,023 B2 | 12/2017 | Hall et al. |
| 9,895,270 B2 | 2/2018 | Coward et al. |
| 2001/0029956 A1 | 10/2001 | Argenta et al. |
| 2001/0034499 A1 | 10/2001 | Sessions et al. |
| 2002/0022861 A1 | 2/2002 | Jacobs et al. |
| 2002/0077661 A1 | 6/2002 | Saadat |
| 2002/0161346 A1 | 10/2002 | Lockwood et al. |
| 2003/0065360 A1 | 4/2003 | Jacobs et al. |
| 2003/0114816 A1 | 6/2003 | Underhill et al. |
| 2003/0114818 A1 | 6/2003 | Benecke et al. |
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0220660 A1 | 11/2003 | Kortenbach et al. |
| 2004/0006319 A1 | 1/2004 | Lina et al. |
| 2004/0010275 A1 | 1/2004 | Jacobs et al. |
| 2004/0054346 A1 | 3/2004 | Zhu et al. |
| 2004/0064132 A1 | 4/2004 | Boehringer et al. |
| 2004/0147465 A1 | 7/2004 | Jiang et al. |
| 2004/0162512 A1 | 8/2004 | Liedtke et al. |
| 2004/0267312 A1 | 12/2004 | Kanner et al. |
| 2005/0107731 A1 | 5/2005 | Sessions |
| 2005/0119694 A1 | 6/2005 | Jacobs et al. |
| 2005/0142331 A1 | 6/2005 | Anderson et al. |
| 2005/0182445 A1 | 8/2005 | Zamierowski |
| 2005/0209574 A1* | 9/2005 | Boehringer ....... A61F 13/00068 604/289 |
| 2005/0222613 A1 | 10/2005 | Ryan |
| 2005/0258887 A1 | 11/2005 | Ito et al. |
| 2005/0267424 A1 | 12/2005 | Eriksson et al. |
| 2006/0020269 A1 | 1/2006 | Cheng |
| 2006/0058842 A1 | 3/2006 | Wilke et al. |
| 2006/0064124 A1 | 3/2006 | Zhu et al. |
| 2006/0069357 A1 | 3/2006 | Marasco |
| 2006/0079599 A1 | 4/2006 | Arthur et al. |
| 2006/0135921 A1 | 6/2006 | Wiercinski et al. |
| 2006/0213527 A1 | 9/2006 | Argenta et al. |
| 2006/0217795 A1 | 9/2006 | Besselink et al. |
| 2006/0257457 A1 | 11/2006 | Gorman et al. |
| 2006/0259074 A1 | 11/2006 | Kelleher et al. |
| 2006/0271018 A1 | 11/2006 | Korf |
| 2007/0032755 A1 | 2/2007 | Walsh |
| 2007/0032763 A1 | 2/2007 | Vogel |
| 2007/0038172 A1 | 2/2007 | Zamierowski |
| 2007/0052144 A1 | 3/2007 | Knirck et al. |
| 2007/0104941 A1 | 5/2007 | Kameda et al. |
| 2007/0118096 A1 | 5/2007 | Smith et al. |
| 2007/0123816 A1 | 5/2007 | Zhu et al. |
| 2007/0123973 A1 | 5/2007 | Roth et al. |
| 2007/0129660 A1 | 6/2007 | McLeod et al. |
| 2007/0149910 A1 | 6/2007 | Zocher |
| 2007/0179421 A1 | 8/2007 | Farrow |
| 2007/0185463 A1 | 8/2007 | Mulligan |
| 2007/0213597 A1 | 9/2007 | Wooster |
| 2007/0219513 A1 | 9/2007 | Lina et al. |
| 2007/0282309 A1 | 12/2007 | Bengtson et al. |
| 2007/0282374 A1 | 12/2007 | Sogard et al. |
| 2007/0299541 A1 | 12/2007 | Chernomorsky et al. |
| 2008/0041401 A1 | 2/2008 | Casola et al. |
| 2008/0108977 A1 | 5/2008 | Heaton et al. |
| 2008/0167593 A1 | 7/2008 | Fleischmann |
| 2008/0243096 A1 | 10/2008 | Svedman et al. |
| 2008/0275409 A1 | 11/2008 | Kane et al. |
| 2008/0287973 A1 | 11/2008 | Aster et al. |
| 2008/0306456 A1 | 12/2008 | Riesinger |
| 2009/0005716 A1 | 1/2009 | Abuzaina et al. |
| 2009/0005744 A1 | 1/2009 | Karpowicz et al. |
| 2009/0018578 A1 | 1/2009 | Wilke et al. |
| 2009/0018579 A1 | 1/2009 | Wilke et al. |
| 2009/0043268 A1 | 2/2009 | Eddy et al. |
| 2009/0069760 A1 | 3/2009 | Finklestein |
| 2009/0069904 A1 | 3/2009 | Picha |
| 2009/0093550 A1 | 4/2009 | Rolfes et al. |
| 2009/0099519 A1 | 4/2009 | Kaplan |
| 2009/0105670 A1 | 4/2009 | Bentley et al. |
| 2009/0131888 A1 | 5/2009 | Joshi |
| 2009/0137973 A1 | 5/2009 | Karpowicz et al. |
| 2009/0204423 A1 | 8/2009 | Degheest et al. |
| 2009/0227938 A1 | 9/2009 | Fasching et al. |
| 2009/0246238 A1 | 10/2009 | Gorman et al. |
| 2009/0259203 A1 | 10/2009 | Hu et al. |
| 2009/0299303 A1 | 12/2009 | Seegert |
| 2009/0299342 A1 | 12/2009 | Cavanaugh, II et al. |
| 2009/0312685 A1 | 12/2009 | Olsen et al. |
| 2010/0022972 A1 | 1/2010 | Lina et al. |
| 2010/0022990 A1 | 1/2010 | Karpowicz et al. |
| 2010/0028407 A1 | 2/2010 | Del Priore et al. |
| 2010/0030132 A1 | 2/2010 | Niezgoda et al. |
| 2010/0036333 A1 | 2/2010 | Schenk, III |
| 2010/0036334 A1 | 2/2010 | Heagle et al. |
| 2010/0047324 A1 | 2/2010 | Fritz et al. |
| 2010/0081983 A1 | 4/2010 | Zocher et al. |
| 2010/0100063 A1 | 4/2010 | Joshi et al. |
| 2010/0106184 A1 | 4/2010 | Coward et al. |
| 2010/0121286 A1 | 5/2010 | Locke et al. |
| 2010/0121287 A1 | 5/2010 | Smith et al. |
| 2010/0137775 A1 | 6/2010 | Hu et al. |
| 2010/0137890 A1 | 6/2010 | Martinez et al. |
| 2010/0150991 A1 | 6/2010 | Bernstein |
| 2010/0160874 A1 | 6/2010 | Robinson et al. |
| 2010/0160876 A1 | 6/2010 | Robinson et al. |
| 2010/0160901 A1 | 6/2010 | Hu et al. |
| 2010/0179515 A1 | 7/2010 | Swain et al. |
| 2010/0198128 A1 | 8/2010 | Turnlund et al. |

(56) References Cited

U.S. PATENT DOCUMENTS

| | | |
|---|---|---|
| 2010/0211030 A1 | 8/2010 | Turner et al. |
| 2010/0256672 A1 | 10/2010 | Weinberg et al. |
| 2010/0262092 A1 | 10/2010 | Hartwell |
| 2010/0262126 A1 | 10/2010 | Hu et al. |
| 2010/0280468 A1 | 11/2010 | Haggstrom et al. |
| 2010/0292717 A1 | 11/2010 | Petter-Puchner et al. |
| 2010/0305490 A1 | 12/2010 | Coulthard et al. |
| 2010/0312159 A1 | 12/2010 | Aali et al. |
| 2011/0004173 A1 | 1/2011 | Hu et al. |
| 2011/0009838 A1 | 1/2011 | Greener |
| 2011/0015594 A1 | 1/2011 | Hu et al. |
| 2011/0021965 A1 | 1/2011 | Karp et al. |
| 2011/0022082 A1 | 1/2011 | Burke et al. |
| 2011/0054283 A1 | 3/2011 | Shuler |
| 2011/0059291 A1 | 3/2011 | Boyce et al. |
| 2011/0060204 A1 | 3/2011 | Weston et al. |
| 2011/0066096 A1 | 3/2011 | Svedman |
| 2011/0077605 A1 | 3/2011 | Karpowicz et al. |
| 2011/0082480 A1 | 4/2011 | Viola |
| 2011/0105963 A1 | 5/2011 | Hu et al. |
| 2011/0106026 A1 | 5/2011 | Wu et al. |
| 2011/0110996 A1 | 5/2011 | Schoenberger et al. |
| 2011/0112458 A1 | 5/2011 | Holm et al. |
| 2011/0130774 A1 | 6/2011 | Criscuolo et al. |
| 2011/0172760 A1 | 7/2011 | Anderson |
| 2011/0178451 A1 | 7/2011 | Robinson et al. |
| 2011/0213319 A1 | 9/2011 | Blott et al. |
| 2011/0224631 A1 | 9/2011 | Simmons et al. |
| 2011/0224632 A1 | 9/2011 | Zimnitsky et al. |
| 2011/0224634 A1 | 9/2011 | Locke et al. |
| 2011/0236460 A1 | 9/2011 | Stopek et al. |
| 2011/0238026 A1 | 9/2011 | Zhang et al. |
| 2011/0238095 A1 | 9/2011 | Browning |
| 2011/0238110 A1 | 9/2011 | Wilke et al. |
| 2011/0245682 A1 | 10/2011 | Robinson et al. |
| 2011/0245788 A1 | 10/2011 | Marquez Canada |
| 2011/0264138 A1 | 10/2011 | Avelar et al. |
| 2011/0275964 A1 | 11/2011 | Greener |
| 2011/0282136 A1 | 11/2011 | Browning |
| 2011/0282309 A1 | 11/2011 | Adie et al. |
| 2011/0282310 A1 | 11/2011 | Boehringer et al. |
| 2011/0305736 A1 | 12/2011 | Wieland et al. |
| 2011/0313374 A1 | 12/2011 | Lockwood et al. |
| 2012/0004631 A9 | 1/2012 | Hartwell |
| 2012/0010637 A1 | 1/2012 | Stopek et al. |
| 2012/0016321 A1 | 1/2012 | Wu et al. |
| 2012/0016322 A1 | 1/2012 | Coulthard et al. |
| 2012/0029449 A1 | 2/2012 | Khosrowshahi |
| 2012/0029455 A1 | 2/2012 | Perez-Foullerat et al. |
| 2012/0035560 A1 | 2/2012 | Eddy et al. |
| 2012/0041402 A1 | 2/2012 | Greener |
| 2012/0059399 A1 | 3/2012 | Hoke et al. |
| 2012/0059412 A1 | 3/2012 | Fleischmann |
| 2012/0065664 A1 | 3/2012 | Avitable et al. |
| 2012/0071841 A1 | 3/2012 | Bengtson |
| 2012/0083755 A1 | 4/2012 | Lina et al. |
| 2012/0095426 A1 | 4/2012 | Visscher et al. |
| 2012/0109188 A1 | 5/2012 | Viola |
| 2012/0116334 A1 | 5/2012 | Albert et al. |
| 2012/0121556 A1 | 5/2012 | Fraser et al. |
| 2012/0123358 A1 | 5/2012 | Hall et al. |
| 2012/0130327 A1 | 5/2012 | Marquez Canada |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0143158 A1 | 6/2012 | Yang et al. |
| 2012/0144989 A1 | 6/2012 | Du Plessis et al. |
| 2012/0150133 A1 | 6/2012 | Heaton et al. |
| 2012/0157942 A1 | 6/2012 | Weston |
| 2012/0172778 A1 | 7/2012 | Rastegar et al. |
| 2012/0172926 A1 | 7/2012 | Hotter |
| 2012/0191054 A1 | 7/2012 | Kazala, Jr. et al. |
| 2012/0191132 A1 | 7/2012 | Sargeant |
| 2012/0197415 A1 | 8/2012 | Montanari et al. |
| 2012/0203189 A1 | 8/2012 | Barta et al. |
| 2012/0209226 A1 | 8/2012 | Simmons et al. |
| 2012/0209227 A1* | 8/2012 | Dunn .................. A61M 1/008 604/319 |
| 2012/0220968 A1 | 8/2012 | Confalone et al. |
| 2012/0222687 A1 | 9/2012 | Czajka, Jr. et al. |
| 2012/0238931 A1 | 9/2012 | Rastegar et al. |
| 2012/0253302 A1 | 10/2012 | Corley |
| 2012/0277773 A1 | 11/2012 | Sargeant et al. |
| 2012/0302440 A1 | 11/2012 | Theliander et al. |
| 2013/0012891 A1 | 1/2013 | Gross et al. |
| 2013/0023842 A1 | 1/2013 | Song |
| 2013/0066365 A1 | 3/2013 | Belson et al. |
| 2013/0096518 A1 | 4/2013 | Hall et al. |
| 2013/0110058 A1 | 5/2013 | Adie et al. |
| 2013/0110066 A1 | 5/2013 | Sharma et al. |
| 2013/0131564 A1 | 5/2013 | Locke et al. |
| 2013/0138054 A1 | 5/2013 | Fleischmann |
| 2013/0150813 A1 | 6/2013 | Gordon et al. |
| 2013/0150814 A1 | 6/2013 | Buan |
| 2013/0190705 A1 | 7/2013 | Vess et al. |
| 2013/0197457 A1 | 8/2013 | Kazala, Jr. et al. |
| 2013/0204213 A1 | 8/2013 | Heagle et al. |
| 2013/0245527 A1 | 9/2013 | Croizat et al. |
| 2013/0253401 A1 | 9/2013 | Locke et al. |
| 2013/0310781 A1 | 11/2013 | Phillips et al. |
| 2013/0325142 A1 | 12/2013 | Hunter et al. |
| 2013/0331757 A1 | 12/2013 | Belson |
| 2014/0068914 A1 | 3/2014 | Coward et al. |
| 2014/0088455 A1 | 3/2014 | Christensen et al. |
| 2014/0094730 A1 | 4/2014 | Greener et al. |
| 2014/0109560 A1 | 4/2014 | Ilievski et al. |
| 2014/0163415 A1 | 6/2014 | Zaiken et al. |
| 2014/0180225 A1 | 6/2014 | Dunn et al. |
| 2014/0180229 A1 | 6/2014 | Fuller et al. |
| 2014/0194836 A1 | 7/2014 | Kazala, Jr. et al. |
| 2014/0194837 A1 | 7/2014 | Robinson et al. |
| 2014/0195004 A9 | 7/2014 | Engqvist et al. |
| 2014/0213994 A1 | 7/2014 | Hardman et al. |
| 2014/0228789 A1 | 8/2014 | Wilkes et al. |
| 2014/0249495 A1 | 9/2014 | Mumby et al. |
| 2014/0316359 A1 | 10/2014 | Collinson et al. |
| 2014/0343518 A1 | 11/2014 | Riesinger |
| 2015/0005722 A1 | 1/2015 | Hu et al. |
| 2015/0025484 A1 | 1/2015 | Simmons et al. |
| 2015/0030806 A1 | 1/2015 | Fink |
| 2015/0057762 A1 | 2/2015 | Harms et al. |
| 2015/0065805 A1 | 3/2015 | Edmondson et al. |
| 2015/0065968 A1 | 3/2015 | Sealy et al. |
| 2015/0080947 A1 | 3/2015 | Greener et al. |
| 2015/0100008 A1 | 4/2015 | Chatterjee |
| 2015/0112290 A1 | 4/2015 | Dunn |
| 2015/0112311 A1 | 4/2015 | Hammond et al. |
| 2015/0119837 A1 | 4/2015 | Thompson, Jr. et al. |
| 2015/0148760 A1 | 5/2015 | Dodd et al. |
| 2015/0150729 A1 | 6/2015 | Dagger et al. |
| 2015/0157758 A1 | 6/2015 | Blücher et al. |
| 2015/0174304 A1 | 6/2015 | Askem et al. |
| 2015/0190288 A1 | 7/2015 | Dunn et al. |
| 2015/0196431 A1 | 7/2015 | Dunn et al. |
| 2015/0216732 A1 | 8/2015 | Hartwell et al. |
| 2016/0144085 A1 | 5/2016 | Melin et al. |
| 2016/0184496 A1 | 6/2016 | Jaecklein et al. |
| 2017/0065751 A1 | 3/2017 | Toth et al. |

FOREIGN PATENT DOCUMENTS

| | | |
|---|---|---|
| CN | 101112326 A | 1/2008 |
| CN | 101744688 A | 6/2010 |
| CN | 201519362 U | 7/2010 |
| CN | 102038575 A | 5/2011 |
| CN | 202568632 U | 12/2012 |
| CN | 103071197 A | 5/2013 |
| CN | 203408163 U | 1/2014 |
| DE | 2949920 A1 | 3/1981 |
| DE | 102005007016 A1 | 8/2006 |
| EP | 1320342 A1 | 6/2003 |
| EP | 2279016 A1 | 2/2011 |
| EP | 2366721 A1 | 9/2011 |
| EP | 2368523 A1 | 9/2011 |

(56) References Cited

FOREIGN PATENT DOCUMENTS

| | | |
|---|---|---|
| EP | 2404626 A2 | 1/2012 |
| EP | 2341955 B1 | 12/2012 |
| EP | 2563421 A1 | 3/2013 |
| EP | 2567682 A1 | 3/2013 |
| EP | 2567717 A1 | 3/2013 |
| EP | 2594299 A2 | 5/2013 |
| EP | 2601984 A2 | 6/2013 |
| EP | 2623137 A2 | 8/2013 |
| EP | 2367517 A4 | 9/2013 |
| EP | 2759265 A2 | 7/2014 |
| EP | 2829287 A1 | 1/2015 |
| EP | 3225261 A1 | 10/2017 |
| GB | 2389794 A | 12/2003 |
| GB | 2423019 A | 8/2006 |
| GB | 2489947 A | 10/2012 |
| GB | 2496310 A | 5/2013 |
| JP | S6257560 A | 3/1987 |
| JP | 2006528038 A | 12/2006 |
| JP | 2009525087 A | 7/2009 |
| JP | 2012-105840 A | 6/2012 |
| RU | 1818103 A1 | 5/1993 |
| RU | 62504 U1 | 4/2007 |
| WO | WO 01/85248 A1 | 11/2001 |
| WO | WO 01/89392 A2 | 11/2001 |
| WO | WO 02/05737 A1 | 1/2002 |
| WO | WO 03/003948 A1 | 1/2003 |
| WO | WO-03049598 A2 | 6/2003 |
| WO | WO 2004/018020 A1 | 3/2004 |
| WO | WO 2004/037334 A1 | 5/2004 |
| WO | WO 2005/046761 A1 | 5/2005 |
| WO | WO 2005/105174 A1 | 11/2005 |
| WO | WO 2006/041496 A1 | 4/2006 |
| WO | WO 2006/046060 A2 | 5/2006 |
| WO | WO 2007//030601 A2 | 3/2007 |
| WO | WO 2007//133618 A2 | 11/2007 |
| WO | WO 2008/027449 A2 | 3/2008 |
| WO | WO 2008/039223 A1 | 4/2008 |
| WO | WO 2008/064502 A1 | 6/2008 |
| WO | WO 2008/091521 A2 | 7/2008 |
| WO | WO 2008/104609 A1 | 9/2008 |
| WO | WO 2009/019495 A1 | 2/2009 |
| WO | WO 2009/071926 A1 | 6/2009 |
| WO | WO 2009/071933 A2 | 6/2009 |
| WO | WO 2009/112062 A1 | 9/2009 |
| WO | WO 2009/112848 A1 | 9/2009 |
| WO | WO 2009/114624 A2 | 9/2009 |
| WO | WO 2009/156709 A1 | 12/2009 |
| WO | WO 2009/158132 A1 | 12/2009 |
| WO | WO 2010/033725 A2 | 3/2010 |
| WO | WO 2010/051073 A1 | 5/2010 |
| WO | WO 2010/059612 A2 | 5/2010 |
| WO | WO 2010/075180 A2 | 7/2010 |
| WO | WO 2010/078349 A2 | 7/2010 |
| WO | WO 2010/092334 A1 | 8/2010 |
| WO | WO 2010/097570 A1 | 9/2010 |
| WO | WO 2010/147535 A1 | 12/2010 |
| WO | WO 2011/023384 A1 | 3/2011 |
| WO | WO 2011/087871 A2 | 7/2011 |
| WO | WO 2011/091169 A1 | 7/2011 |
| WO | WO 2011/106722 A1 | 9/2011 |
| WO | WO 2011/115908 A1 | 9/2011 |
| WO | WO 2011/135284 A1 | 11/2011 |
| WO | WO 2011/135286 A1 | 11/2011 |
| WO | WO 2011/135287 A1 | 11/2011 |
| WO | WO 2011/137230 A1 | 11/2011 |
| WO | WO 2011/144888 A1 | 11/2011 |
| WO | WO 2012/021553 A1 | 2/2012 |
| WO | WO 2012/038727 A2 | 3/2012 |
| WO | WO 2012/069793 A1 | 5/2012 |
| WO | WO 2012/082716 A2 | 6/2012 |
| WO | WO 2012/082876 A1 | 6/2012 |
| WO | WO 2012/087376 A1 | 6/2012 |
| WO | WO 2012/106590 A2 | 8/2012 |
| WO | WO 2012/112204 A1 | 8/2012 |
| WO | WO 2012/136707 A1 | 10/2012 |
| WO | WO 2012/142473 A1 | 10/2012 |
| WO | WO 2012/156655 A1 | 11/2012 |
| WO | WO 2012/168678 A1 | 12/2012 |
| WO | WO 2013/007973 A2 | 1/2013 |
| WO | WO 2013/012381 A1 | 1/2013 |
| WO | WO 2013/043258 A1 | 3/2013 |
| WO | WO 2013/071243 A2 | 5/2013 |
| WO | WO 2013/076450 A1 | 5/2013 |
| WO | WO 2013/079947 A1 | 6/2013 |
| WO | WO 2013/175309 A1 | 11/2013 |
| WO | WO 2013/175310 A2 | 11/2013 |
| WO | WO 2014/013348 A2 | 1/2014 |
| WO | WO 2014/014842 A1 | 1/2014 |
| WO | WO 2014/014871 A1 | 1/2014 |
| WO | WO 2014/014922 A1 | 1/2014 |
| WO | WO 2014/020443 A2 | 2/2014 |
| WO | WO 2014/024048 A1 | 2/2014 |
| WO | WO 2014/140578 A1 | 9/2014 |
| WO | WO 2014/158526 A1 | 10/2014 |
| WO | WO 2014/165275 A1 | 10/2014 |
| WO | WO-2014178945 A1 | 11/2014 |
| WO | WO 2014/194786 A1 | 12/2014 |
| WO | WO 2015/008054 A1 | 1/2015 |
| WO | WO 2015/061352 A2 | 4/2015 |
| WO | WO 2015/109359 A1 | 7/2015 |
| WO | WO 2015/110409 A1 | 7/2015 |
| WO | WO 2015/110410 A1 | 7/2015 |

OTHER PUBLICATIONS

"Definition of Adhere," The Free Dictionary, accessed on Mar. 23, 2017 from http://www.thefreedictionary.com/adhere, 6 pages.
"Definition of Oculiform," Webster's Revised Unabridged Dictionary, accessed from the Free Dictionary on May 30, 2018 from URL: https://www.thefreedictionary.com/Oculiform, 1913, 1 page.
"Definition of Throughout," Merriam-Webster Dictionary, accessed on Aug. 29, 2017 from https://www.merriam-webster.com/dictionary/throughout, 11 pages.
Hougaard, et al., "The Open Abdomen: Temporary Closure with a Modified Negative Pressure Therapy Technique," International Wound Journal, ISSN 1742-4801, 2014, pp. 13-16.
International Preliminary Report on Patentability for Application No. PCT/GB2014/050746, dated Sep. 15, 2015, 7 pages.
International Search Report for Application No. PCT/GB2014/050746, dated Jun. 24, 2014, 3 pages.
Kapischke M., et al., "Self-Fixating Mesh for the Lichtenstein Procedure—a Prestudy," Langenbecks Arch Surg, 2010, vol. 395, pp. 317-322.

* cited by examiner

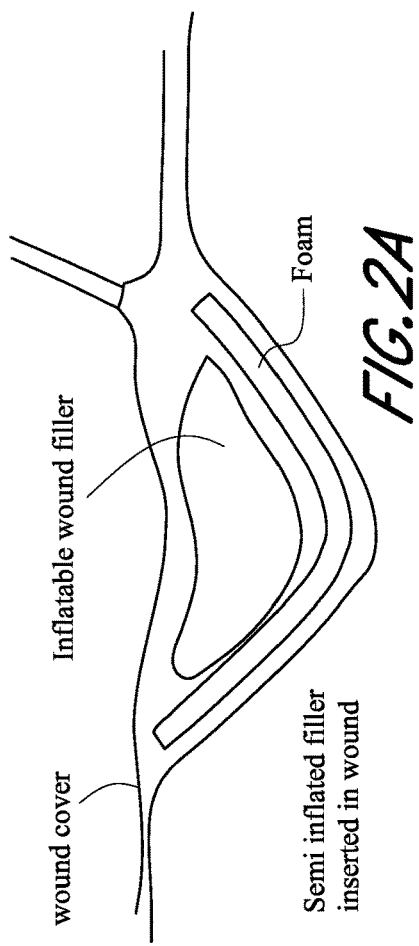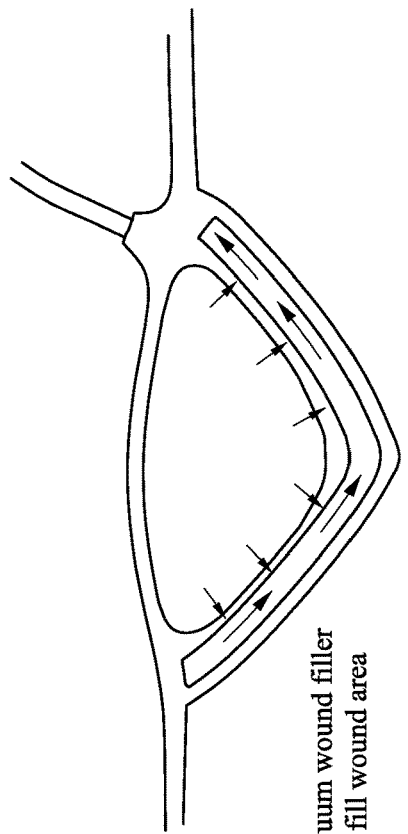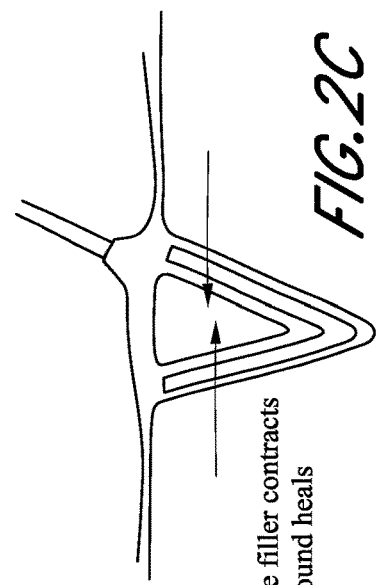

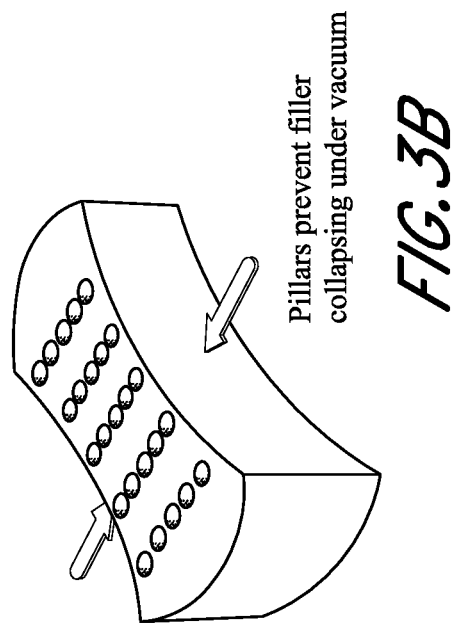
FIG. 3B Pillars prevent filler collapsing under vacuum
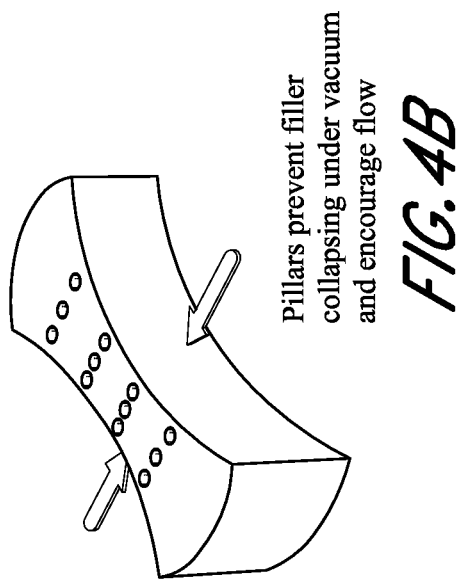
FIG. 4B Pillars prevent filler collapsing under vacuum and encourage flow
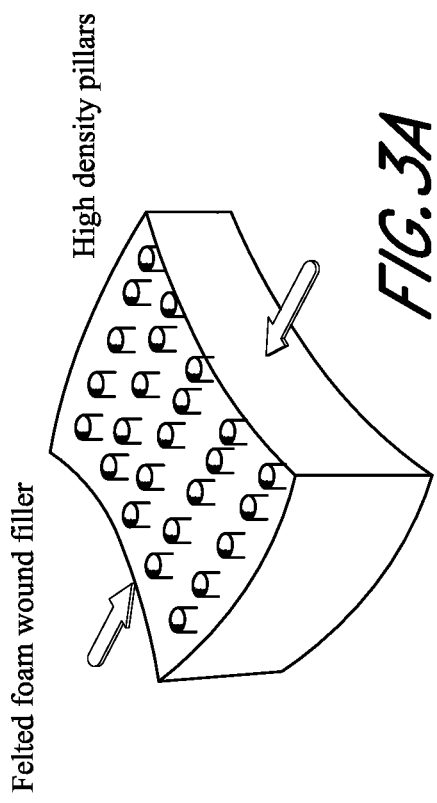
FIG. 3A High density pillars / Felted foam wound filler
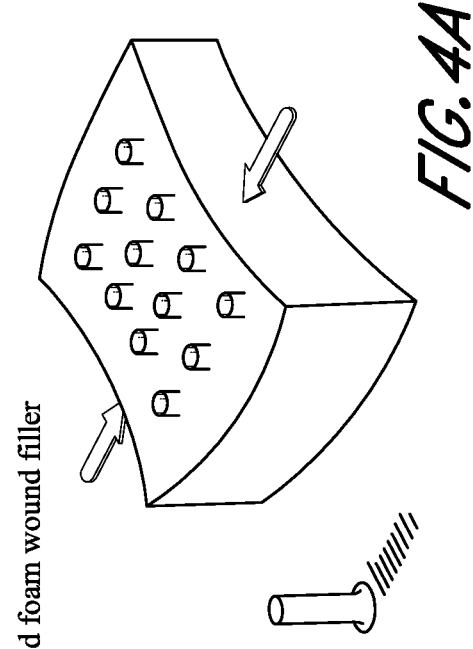
FIG. 4A Felted foam wound filler

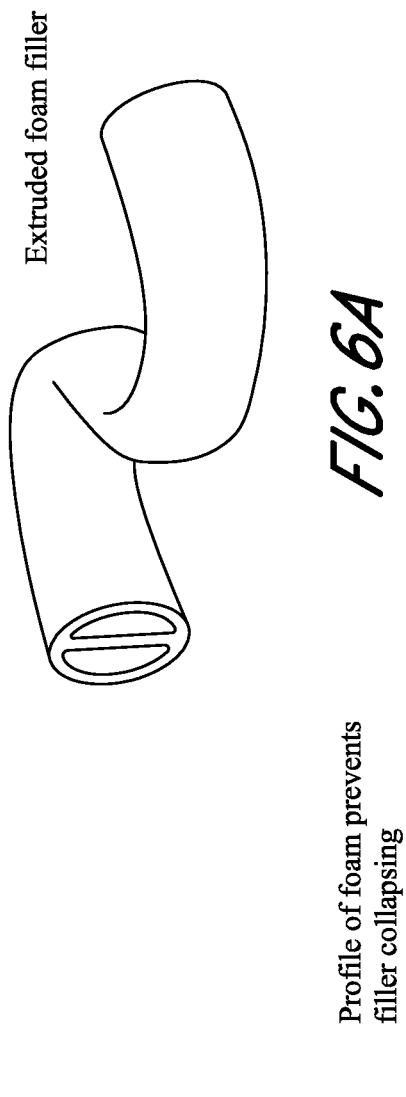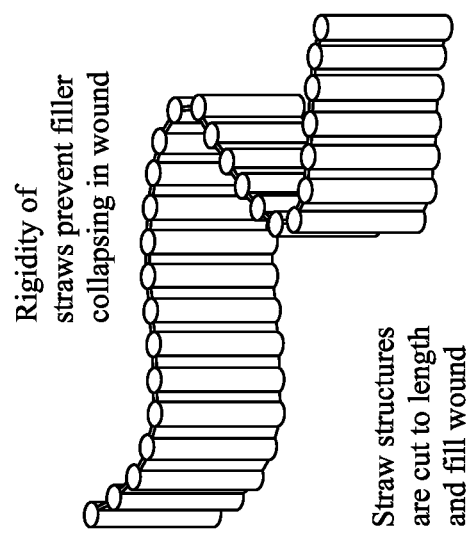
FIG. 6A Extruded foam filler
FIG. 6C
FIG. 6B Outer features grip to edge of wound / Profile of foam prevents filler collapsing
FIG. 5A Rigidity of straws prevent filler collapsing in wound / Straw structures are cut to length and fill wound
FIG. 5B

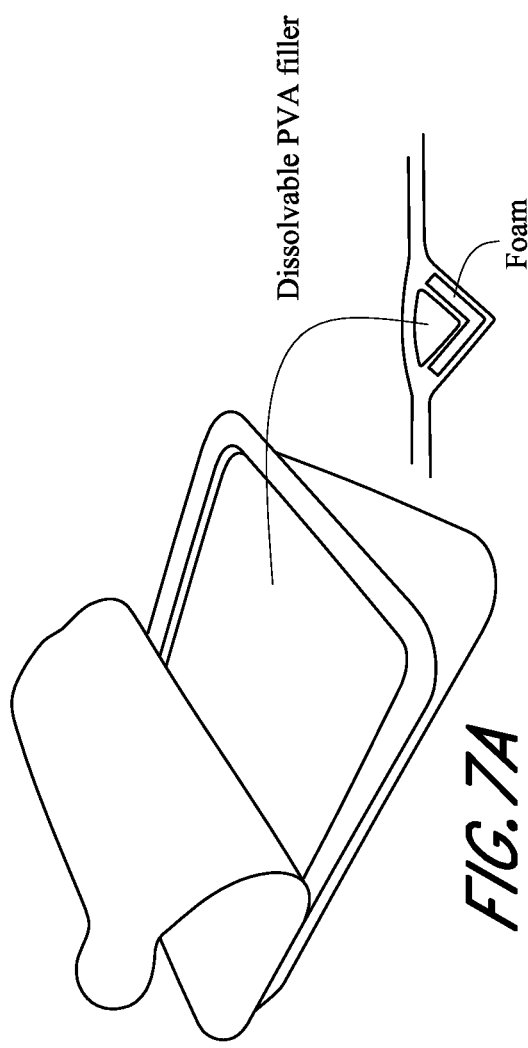
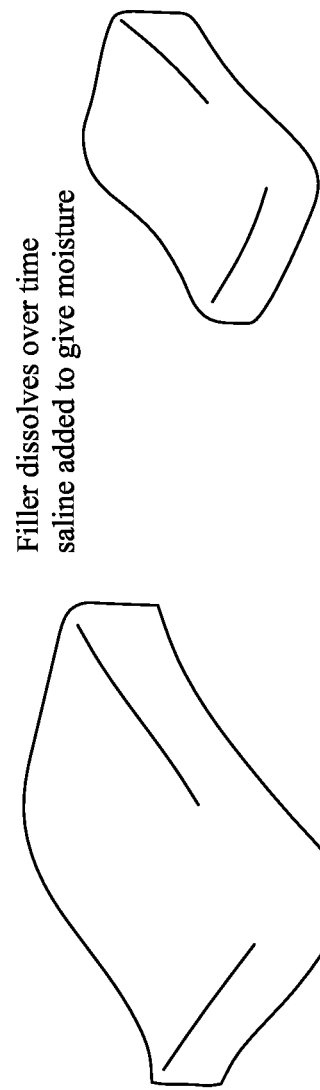
FIG. 7A
FIG. 7B
FIG. 7C

Variable resorption rates allow filler to dissolve as wound heals

Rigid foam wound filler

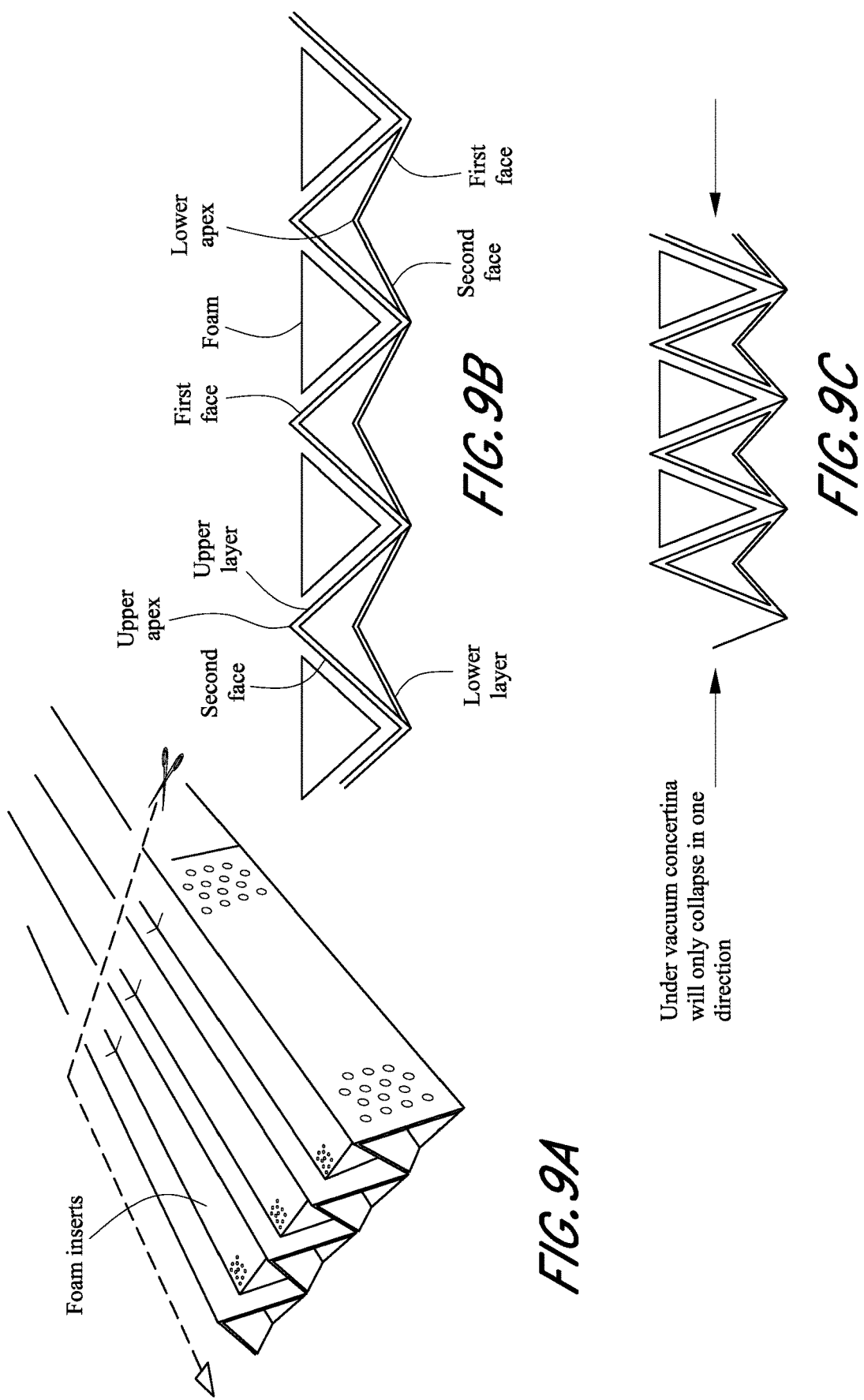

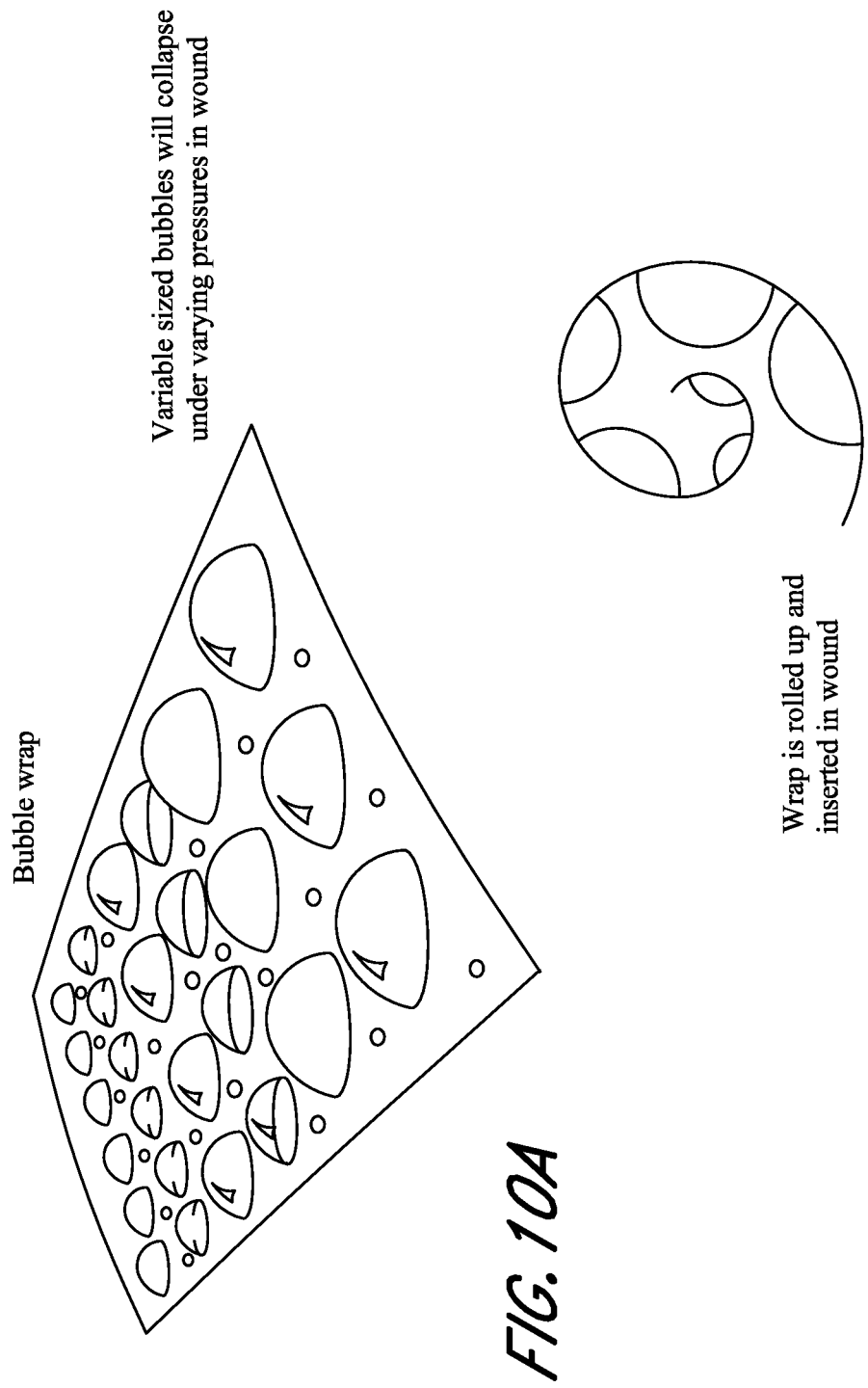

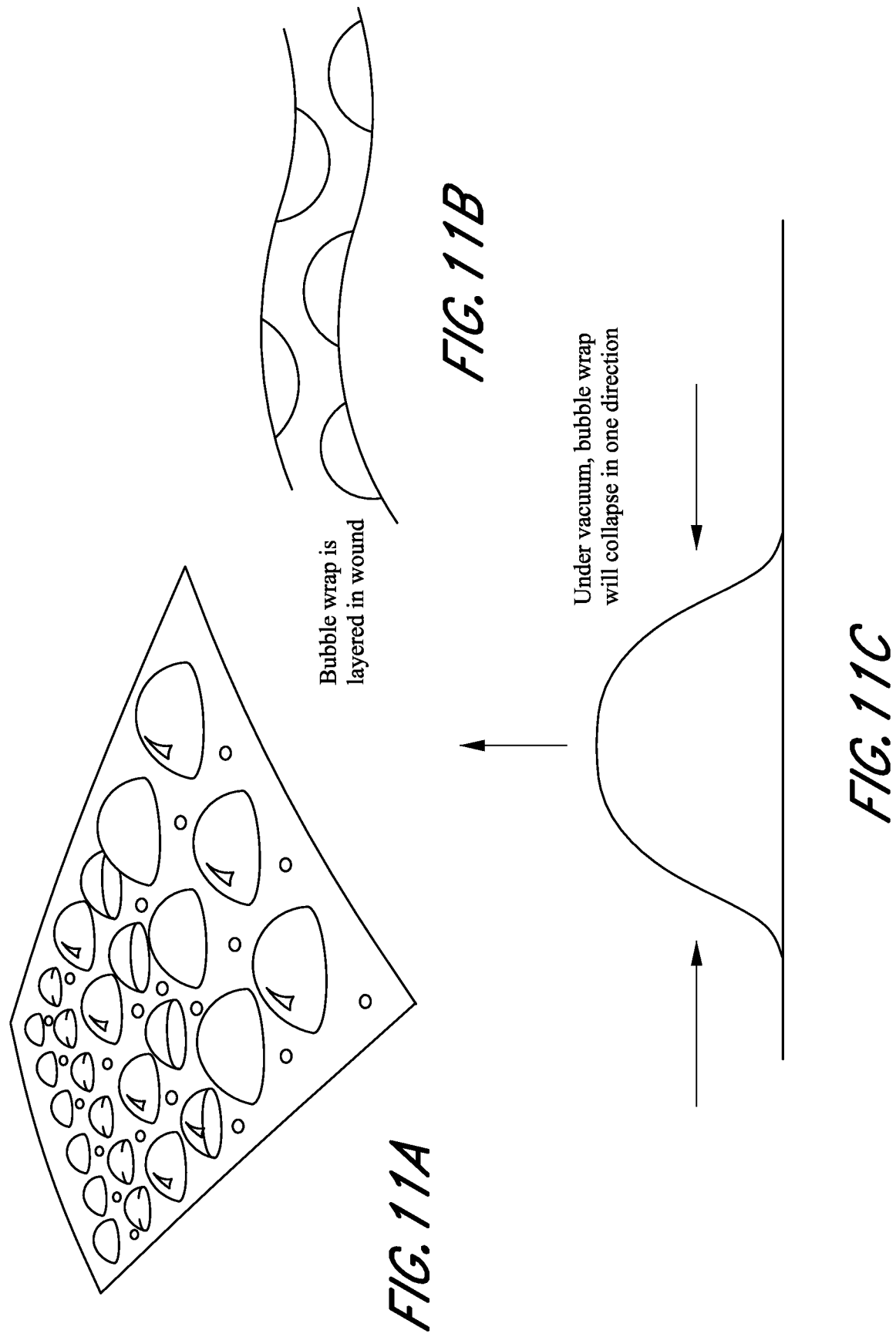

COMPRESSIBLE WOUND FILLERS AND SYSTEMS AND METHODS OF USE IN TREATING WOUNDS WITH NEGATIVE PRESSURE

CROSS-REFERENCE TO RELATED APPLICATIONS

This application is a continuation of U.S. application Ser. No. 14/774,695, filed Sep. 10, 2015, which is a national stage application of International Patent Application No. PCT/GB2014/050746, filed on Mar. 13, 2014, which claims the benefit of U.S. Provisional Application No. 61/784,868, filed Mar. 14, 2013, entitled COMPRESSIBLE WOUND FILLERS AND SYSTEMS AND METHODS OF USE IN TREATING WOUNDS WITH NEGATIVE PRESSURE. The content of the aforementioned application is hereby incorporated by reference in its entirety as if fully set forth herein. The benefit of priority to the foregoing applications is claimed under the appropriate legal basis, including, without limitation, under 35 U.S.C. § 119(e).

BACKGROUND OF THE INVENTION

Field of the Invention

Embodiments described herein relate to devices and methods that can be used to treat a wound with negative pressure. Particular embodiments can also be useful to aid in wound closure, for example in abdominal wounds.

SUMMARY OF THE INVENTION

Generally, the embodiments described herein can be used to assist in the treatment of wounds with negative pressure. The embodiments can be particularly useful in treating large wounds, such as abdominal wounds, where closure and approximation of the wound edges is challenging. Certain embodiments described herein are directed to the compressible wound fillers, their methods of use and systems incorporating the same, wherein the compressible wound filler is configured to compress or collapse, for example horizontally, as the wound closes under negative pressure.

In some embodiments, a method of treating a wound comprises:
placing a porous wound contacting layer, for example foam, in a wound;
positioning an inflatable wound filler over the porous wound contacting layer, wherein the inflatable wound filler may be semi-inflated, the inflatable wound filler comprising a plurality of pores configured to allow the passage of fluid;
positioning at least one wound cover over the inflatable wound filler to form a seal with skin surrounding the wound;
applying negative pressure to the wound, wherein the application of negative pressure causes the inflatable wound filler to further inflate; and
releasing fluid from the inflatable wound filler, wherein the release of fluid from the inflatable wound filler causes the inflatable wound filler to contract and draw the edges of the wound closer together.

In certain embodiments, a negative pressure treatment apparatus may comprise a porous wound contacting layer, an inflatable wound filler, a wound cover and a source of negative pressure configured to perform the method as described above.

In some embodiments, a wound treatment apparatus for use with negative pressure comprises any of a number of wound fillers, as described herein. In some embodiments, the wound treatment apparatus may further comprise a cover configured to be placed over the wound filler and seal to skin surrounding the wound. In certain embodiments, the wound treatment apparatus may further comprise a port configured to connect the wound cover to a source of negative pressure. In further embodiments, the wound treatment apparatus may comprise a source of negative pressure configured to provide negative pressure to the wound.

In some embodiments, a wound filler for use in treating a wound with negative pressure can comprise:
a porous wound filling material;
a plurality of vertically extending members configured to extend vertically when the wound filler is positioned within a wound bed, the vertically extending members being made of a more rigid material than the porous wound filling material; and
wherein upon application of negative pressure to the wound filler, the wound filler is configured to contract horizontally with the vertically extending members reducing vertical movement of the wound filler.

In some embodiments, a wound filler for use in treating a wound with negative pressure can comprise:
a plurality of vertically extending straws configured to extend vertically when the wound filler is positioned within a wound bed;
a plurality of joints connecting adjacent vertically extending straws; and
wherein upon application of negative pressure to the wound filler, the wound filler is configured to contract horizontally with the vertically extending straws reducing vertical movement of the wound filler.

In some embodiments, the vertically extending straws may be solid. In certain embodiments the straws can be hollow. Some embodiments may call for the joints to be flexible and/or rigid. In certain embodiments, the wound filler may be further configured to be placed in the wound bed in a spiral conformation. In particular embodiments, a wound treatment apparatus may further comprise at least one pressure sensor.

In some embodiments, a wound filler for use in treating a wound with negative pressure can comprise:
a flexible hollow tube;
a vertical strut positioned within the flexible hollow tube, the vertical strut configured to extend vertically when the wound filler is positioned within a wound bed, the vertical strut being made of a more rigid material than the flexible hollow tube; and
wherein upon application of negative pressure to the wound filler, the wound filler is configured to contract horizontally with the vertically strut reducing vertical movement of the wound filler.

Certain embodiments of the wound treatment apparatus may call for the addition of gripping members located on the outside of the flexible hollow tube, the gripping members configured to grip the wound bed. In some embodiments, the flexible hollow tube may be configured to be placed within the wound bed in a spiral conformation. In some embodiments, the flexible hollow tube comprises an extruded foam.

In some embodiments, a method of treating a wound may comprise:
placing a porous wound contact layer in the wound;
positioning a dissolvable material over the porous wound contact layer, the dissolvable material for example comprising a polyvinyl alcohol; and applying negative pressure to the wound, wherein the application of negative pressure draws moisture from the wound into the dissolvable material, causing the dissolvable material to dissolve.

In certain embodiments, a negative pressure treatment apparatus may comprise a dissolvable material as described above, a wound cover and a source of negative pressure configured to perform the method as described above.

In certain embodiments, a wound filler for use in treating a wound with negative pressure comprises:
one or more rigid concentric rings surrounding a central portion of the wound filler, the concentric rings configured to resorb into a wound; and
wherein the one or more rings comprises an outer ring configured to resorb more quickly than the remaining rings.

In some embodiments, a wound filler for use in treating a wound with negative pressure comprises:
a plurality of elongate upper layers, wherein the upper layers are connected at an upper apex at a first angle;
a plurality of elongate lower layers, wherein the lower layers are connected at a lower apex at a second angle;
wherein the upper layers and the lower layers are connected to form a pattern of repeating, parallel rows;
wherein the second angle is greater than the first angle; and
wherein upon application of negative pressure to the wound filler, the wound filler is configured to collapse in a horizontal direction while remaining rigid in a vertical direction.

In certain embodiments, a wound filler for use in treating a wound with negative pressure may comprise:
a layer comprising a plurality of variable size bubbles spread across a surface of the layer; and
wherein the bubbles are configured to collapse under negative pressure.

In certain embodiments, a wound filler for use in treating a wound with negative pressure can comprise:
a plurality of layers comprising bubbles, wherein the layers are configured such that the bubbles face one another; and
wherein upon application of negative pressure to the wound filler, the bubbles are configured to collapse in a horizontal direction while remaining rigid in a vertical direction.

In some embodiments, a method of treating a wound comprises:
placing a wound filler into the wound;
applying a cover over the wound filler and sealing the cover to skin surrounding the wound;
applying negative pressure to the wound through the cover; and
controlling collapse of the wound filler as the wound closes under negative pressure.

Some embodiments may call for the addition of a pressure sensor to monitor an internal pressure. In certain embodiments, the internal pressure may be measured by monitoring at least one of a bladder pressure, an aortic pressure, a pressure within the colon, a pressure within the uterus, a limb pressure, and a blood flow rate. In certain embodiments, the wound filler may be an inflatable bladder, and controlling collapse of the wound filler comprises controlling the pressure within the bladder. Some embodiments may call for dynamically adjusting at least one of the volume, stiffness, pressure to collapse the wound filler as the wound closes. In particular embodiments, at least one of the volume, stiffness pressure and collapse of the wound packing member is dynamically adjusted based on internal pressure readings of the patient.

BRIEF DESCRIPTION OF THE DRAWINGS

Embodiments of the present invention will now be described hereinafter, by way of example only, with reference to the accompanying drawings in which:

FIGS. 2A-C illustrates an embodiment of a semi-inflated wound filler.

FIGS. 3A-B illustrate embodiments of a wound filler comprising pillars.

FIGS. 4A-B illustrate embodiments of a wound filler comprising pillars.

FIGS. 5A-B illustrate an embodiment of a wound filler comprising rigid straws.

FIGS. 6A-C illustrate and embodiment of a wound filler comprising an extruded foam.

FIGS. 7A-C illustrate an embodiment of a dissolvable wound filler.

FIGS. 9A-C illustrate embodiments of a wound closure device.

FIGS. 10A-B illustrate an embodiment of a wound filler comprising variable-sized bubbles.

FIGS. 11A-C illustrate an embodiment of a wound filler comprising bubbles that collapse in one direction.

DETAILED DESCRIPTION OF THE PREFERRED EMBODIMENTS

Figure 1:
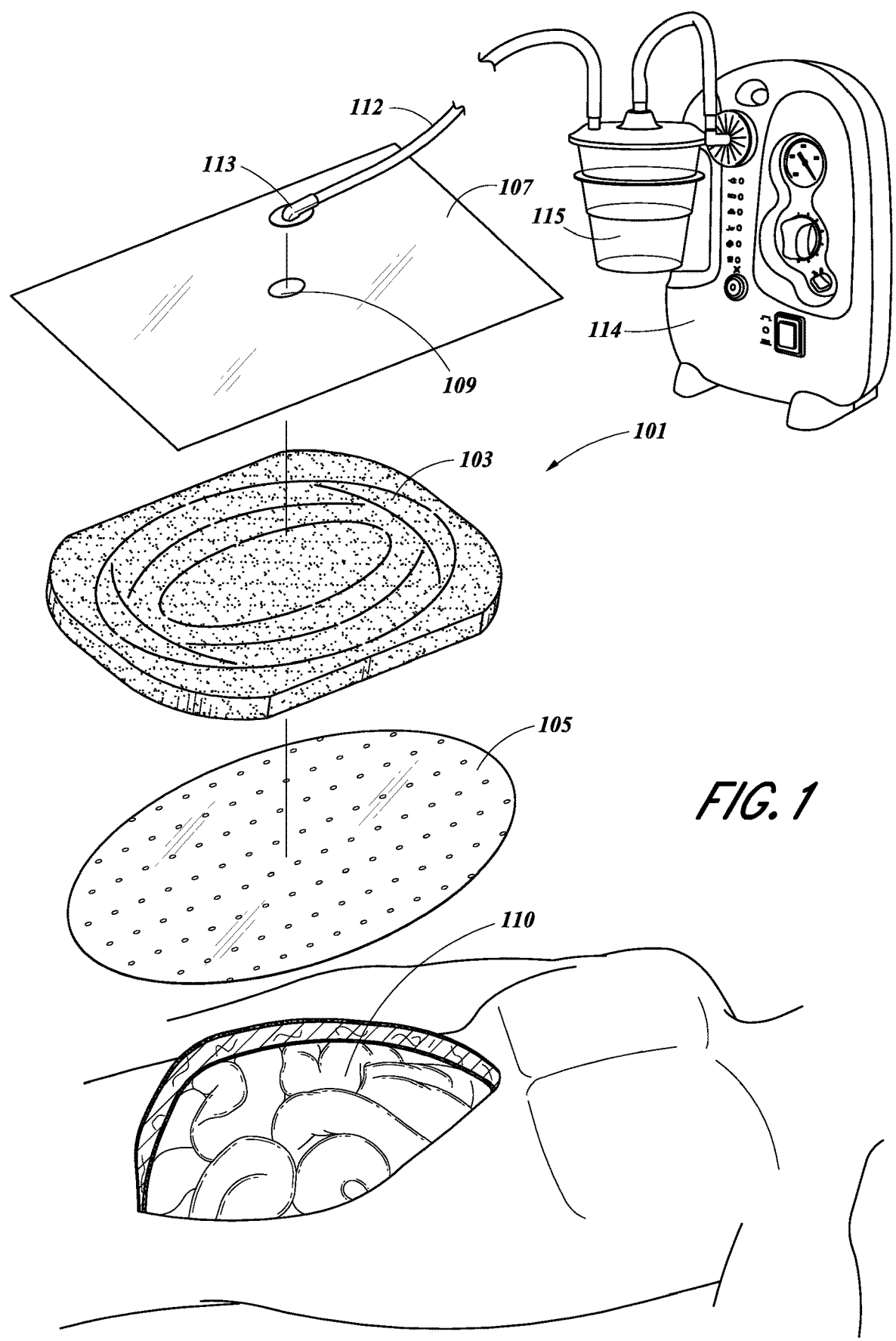
FIG. 1 illustrates an embodiment of a negative pressure wound therapy system.

Various embodiments that can be used for the treatment of wounds will now be described with references to the following figures and description which follow. It will be of course understood that various omissions, substitutions, and changes in the form and details of the embodiments illustrated can be made without departing from the spirit of the disclosure. Additionally, the various features and processes described above can be used independently of one another, or can be combined in various ways. All possible combinations and sub-combinations are intended to fall within the scope of this disclosure. Many of the embodiments described above include similar components, and as such, these similar components can be interchanged in different embodiments.

Embodiments disclosed herein relate to apparatuses and methods of treating a wound with reduced pressure, including pump and wound dressing components and apparatuses. Generally, the embodiments including the wound fillers described herein may be used in combination with a negative pressure system comprising a drape or wound cover placed over the filler. A vacuum source, such as a pump, may be connected to the cover, for example, through one or more tubes connected to an aperture or port made in or under the cover. The apparatuses and components comprising the wound overlay and packing materials, if any, are sometimes collectively referred to herein as dressings. Further details of methods and apparatuses that are usable with the embodiments described herein are found in the following applications, which are hereby incorporated by reference in their entireties: U.S. application Ser. No. 12/886,088, titled "SYSTEMS AND METHODS FOR USING NEGATIVE PRESSURE WOUND THERAPY TO MANAGE OPEN ABDOMINAL WOUNDS", published as US 2011/0213287 on Sep. 1, 2011; U.S. application Ser. No. 13/092,042, titled "WOUND DRESSING AND METHOD OF USE", published as US 2011/0282309 on Nov. 17, 2011.

It will be appreciated that throughout this specification reference is made to a wound or wounds. It is to be understood that the term wound is to be broadly construed and encompasses open and closed wounds in which skin is torn, cut or punctured, or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments, the components of the negative pressure treatment system described herein can be particularly suited for incisional wounds that exude a small amount of wound exudate.

As is used herein, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than −X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The negative pressure range for some embodiments of the present disclosure can be approximately −80 mmHg, or between about −20 mmHg and −200 mmHg. Note that these pressures are relative to normal ambient atmospheric pressure. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

Turning to FIG. 1, treatment of a wound with negative pressure in certain embodiments uses a negative pressure treatment system 101 as illustrated schematically here. In this embodiment, a wound site 110, illustrated here as an abdominal wound site, may benefit from treatment with negative pressure. Such abdominal wound sites may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening—particularly in the abdominal cavity—remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, preferably using the application of negative pressure, can be targeted to minimize the risk of infection, while promoting tissue viability and the removal of deleterious substances from the wound site. The application of reduced or negative pressure to a wound site has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, and/or enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached. Consequently, the application of negative pressure to a wound site 110 can be beneficial to a patient.

Accordingly, certain embodiments provide for a wound contact layer 105 to be placed over the wound site 110. Preferably, the wound contact layer 105 can be a thin, flexible material which will not adhere to the wound site or the exposed viscera in close proximity. For example, polymers such as polyurethane, polyethylene, polytetrafluoroethylene, or blends thereof may be used. In one embodiment, the wound contact layer is permeable. For example, the wound contact layer 105 can be provided with openings, such as holes, slits, or channels, to allow the removal of fluids from the wound site 110 or the transmittal of negative pressure to the wound site 110. Additional embodiments of the wound contact layer 105 are described in further detail below.

Certain embodiments of the negative pressure treatment system 101 may also use a porous wound filler 103, which can be disposed over the wound contact layer 105. This pad 103 can be constructed from a porous material, for example foam, that is soft, resiliently flexible, and generally conformable to the wound site 110. Such a foam can include an open-celled and reticulated foam made, for example, of a polymer. Suitable foams include foams composed of, for example, polyurethane, silicone, and polyvinyl alcohol. Preferably, this pad 103 can channel wound exudate and other fluids through itself when negative pressure is applied to the wound. Some pads 103 may include preformed channels or openings for such purposes. In certain embodiments, the pad 103 may have a thickness between about one inch and about two inches. The pad may also have a length of between about 16 and 17 inches, and a width of between about 11 and 12 inches. In other embodiments, the thickness, width, and/or length can have other suitable values. Other embodiments of wound fillers that may be used in place of or in addition to the pad 103 are discussed in further detail below.

Preferably, a drape 107 is used to seal the wound site 110. The drape 107 can be at least partially liquid impermeable, such that at least a partial negative pressure may be maintained at the wound site. Suitable materials for the drape 107 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the drape may be hydrophobic or hydrophilic. Examples of suitable materials include Transeal® available from DeRoyal and OpSite® available from Smith & Nephew. In order to aid patient comfort and avoid skin maceration, the drapes in certain embodiments are at least partly breathable, such that water vapor is able to pass through without remaining trapped under the dressing. An adhesive layer may be provided on at least a portion the underside of the drape 107 to secure the drape to the skin of the patient, although certain embodiments may instead use a separate adhesive or adhesive strip. Optionally, a release layer may be disposed over the adhesive layer to protect it prior to use and to facilitate handling the drape 107; in some embodiments, the release layer may be composed of multiple sections.

The negative pressure system 101 can be connected to a source of negative pressure, for example a pump 114. One example of a suitable pump is the Renasys EZ pump available from Smith & Nephew. The drape 107 may be connected to the source of negative pressure 114 via a conduit 112. The conduit 112 may be connected to a port 113 situated over an aperture 109 in the drape 107, or else the conduit 112 may be connected directly through the aperture 109 without the use of a port. In a further alternative, the conduit may pass underneath the drape and extend from a side of the drape. U.S. Pat. No. 7,524,315 discloses other similar aspects of negative pressure systems and is hereby incorporated by reference in its entirety and should be considered a part of this specification.

In many applications, a container or other storage unit 115 may be interposed between the source of negative pressure 114 and the conduit 112 so as to permit wound exudate and other fluids removed from the wound site to be stored without entering the source of negative pressure. Certain types of negative pressure sources—for example, peristaltic pumps—may also permit a container 115 to be placed after the pump 114. Some embodiments may also use a filter to prevent fluids, aerosols, and other microbial contaminants from leaving the container 115 and/or entering the source of negative pressure 114. Further embodiments may also include a shut-off valve or occluding hydrophobic and/or oleophobic filter in the container to prevent overflow; other embodiments may include sensing means, such as capacitive sensors or other fluid level detectors that act to stop or shut off the source of negative pressure should the level of fluid in the container be nearing capacity. At the pump exhaust, it may also be preferable to provide an odor filter, such as an activated charcoal canister.

The Wound Fillers and Wound Closure Devices of FIGS. 2A-11C

FIGS. 2A-2C illustrate one embodiment of a wound filler that may be used in the negative pressure systems and methods as described herein. As illustrated in FIG. 2A, a layer of foam or other porous material may be placed in the wound. An inflatable wound filler such as a bag or other structure may be placed in the wound over the porous material. The inflatable wound filler may be placed in the wound in a semi-inflated state. A wound cover may be placed over the wound filler that is sealed to skin surrounding the wound. A conduit may connect the wound cover to a source of negative pressure (not shown). When negative pressure is applied to the wound through the wound cover as shown in FIG. 2B, the increase in vacuum level under the wound cover causes the bag to inflate further (due to the drop in the surrounding pressure). The inflation of the bag provides an upward force against the wound cover to prevent the wound cover from extending downward into the wound. As negative pressure is applied, wound exudate may travel through the porous material to a collection location which may be located either outside the wound cover (such as canister 115 described above) or even to a collection location located under the wound cover.

The inflatable wound filler may comprise at least a portion of porous material, and may for example have a plurality of pores or openings to allow air or other inflation fluid to leak from the inflatable filler. As shown in FIG. 2B, inflation fluid can leak out of the wound filler, and as shown in FIG. 2C, over time the filler contracts as the wound heals due to the leakage of the wound filler, and the inflatable filler will contract to allow the edges and sides of the wound to draw closer together.

FIGS. 3A-4B illustrate embodiments of a porous wound filler material, such as a felted foam wound filler, having a plurality of vertically extending pillars spaced throughout. The pillars may be arranged in parallel rows, and may be approximately equally spaced from each other. In the embodiment of FIGS. 3A-3B, the pillars may be made of a higher density material than that of the porous wound filler material. In some embodiments, the pillars may be arranged in a linear formation within the rows, thereby limiting the amount of collapse due to interaction between the pillars. In certain embodiments, the pillars may be arranged in a staggered formation within the rows, thereby allowing for greater collapse because the pillars will no longer block one another to the same extent. In certain embodiments, the pillars may alternate in their staggered formation one by one, while in other formations the pillars may alternate in two by twos, three by threes, etc.

In the embodiment of FIGS. 4A-4B, the pillars may be rigid cylindrical, hollow members through which fluid can flow. When placed in a wound under negative pressure, the pillars allow the filler to collapse horizontally, but prevent vertical collapse.

FIG. 5A illustrates an embodiment of a wound filler comprising a plurality of vertical straws connected to each other in series side-by-side along the length of the straws to form an elongate strip of material. The straws may be solid or hollow. The elongate strip of material is preferably vertically rigid, but may be flexible about the joints connecting adjacent straws to allow the elongate material to be manipulated to fit into a wound. For example, as shown in FIG. 5B (which shows a top view of a wound), the elongate strip of material can be cut to an appropriate length and may be placed in a wound in a spiral or other desired configuration, with the straws oriented vertically within the wound. The straws may also be compressible in a horizontal direction such that when the wound closes under negative pressure therapy, the straws will collapse horizontally within the wound but remain vertically rigid.

FIGS. 6A-6B illustrate an embodiment of a wound filler comprising an elongate, flexible hollow tube that may be placed in a wound in a desired configuration. As illustrated in FIG. 6C, the hollow tube may be arranged in a spiral configuration into a wound, though other configurations are possible. The tube may be made of an extruded foam or other materials. As illustrated, the tube may include a vertical strut that extends through the middle of the tube to provide the tube with vertical rigidity. In certain embodiments, the wound filler does not contain a vertical strut but still retains vertical rigidity. Additionally, as shown in FIG. 6B, the tube may be made of a material that is horizontally compressible. The tube may also have gripping members that may be used to connect the sides of the tube to other portions of the tube or to the edges of the wound. When the tube is arranged in a wound for negative pressure wound therapy, the vertical strut is preferably arranged vertically in the wound to provide vertical rigidity, while the sides of the tube are configured to horizontally collapse as the wound closes. In certain embodiments, the wound filler comprising an elongate, flexible hollow tube may be inflated.

FIGS. 7A-7C illustrate an embodiment comprises a wound filler made of dissolvable material, such as a dissolvable polyvinyl alcohol (PVA) filler. As illustrated in FIG. 7A, a dissolvable PVA material may be placed in a wound over a porous material (such as foam), where the porous material provides a fluid path. The dissolvable PVA material may be provided in any suitable form, including sheet, rolls, powder, or other configurations. During negative pressure wound treatment, moisture from the wound slowly dissolves the PVA over time, allowing the wound to close. In one embodiment, as illustrated in FIGS. 7B-7C, saline can be introduced to the filler as treatment is occurring to increase and/or control the dissolving of the PVA filler.

Figure 8C:
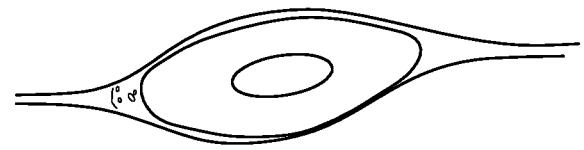
FIGS. 8A-C illustrate an embodiment of a wound filler with various sections having various rates of dissolution.
Figure 8B:
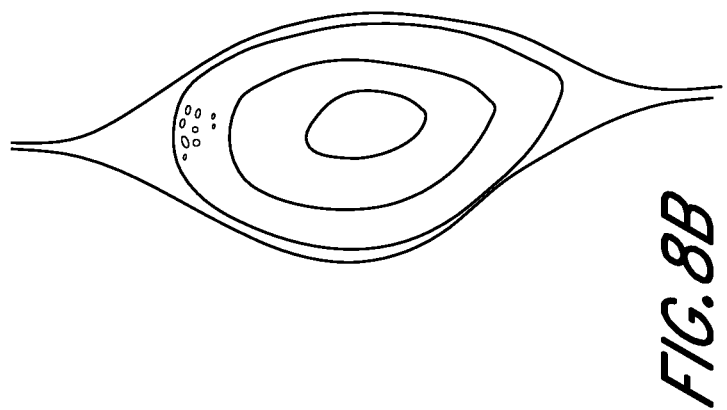
Figure 8A:
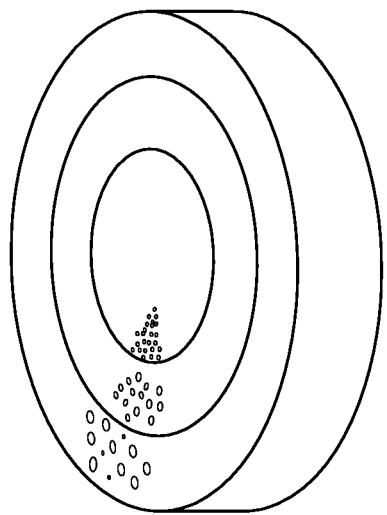

FIGS. 8A-8C illustrate an embodiment of a wound filler comprising one or more concentric rings around a central portion of wound filler. The central portion and one or more rings can be made of rigid material, but may have variable resorption rates. Under negative pressure wound therapy, an outer ring may be configured to dissolve more quickly than an inner ring, as shown in the transition from FIG. 8B to 8C. Thus, as the wound closes, the amount of wound filler decreases to allow the edges of the wound to come closer together.

FIGS. 9A-9C illustrate an embodiment of a wound filler having an accordion or concertina configuration. The wound filler may comprise an upper layer and a lower layer that together form a pattern of repeating, parallel rows. The wound filler may be made of any suitable material, including silicone, rigid plastics, semi-rigid plastics, biocompatible materials, flexible plastic materials, composite materials, and foam. The upper layer of each row comprises a first face and a second face each comprising a generally flat, elongate and rectangular piece of material that are connected at an angle to each other at an upper apex. The lower layer of each row comprises a first face and a second face each comprising a generally flat, elongate and rectangular piece of material that are connected at an angle to each other at a lower apex. As illustrated, the upper apex is generally above the lower apex, and the angle formed between the first and second faces of the lower layer is greater than the angle formed between the first and second faces of the upper layer.

Foam inserts may optionally be provided between adjacent rows of the wound filler. As illustrated in FIG. 9B, the foam inserts may have a triangular shape in cross-section to correspond with the triangular-shaped gap between the first and second faces of the upper layer.

The wound filler and foam inserts may be cut to an appropriate size as shown in FIG. 9A for placement into a wound. A wound cover may be positioned over the wound filler and foam inserts as described above, and negative pressure may be provided to the wound through the wound cover. Under negative pressure, the wound filler may collapse preferably in only one horizontal direction, as shown in FIG. 9C. As the wound filler collapses, the angle at the upper and lower apices decreases and the faces in each row come closer together. The foam inserts may be compressed between the first and second faces of the upper layer as negative pressure is applied, and desirably can be selected to control the amount of compression of the wound filler as the wound filler compresses when the wound closes under negative pressure.

FIGS. 10A-10B illustrate an embodiment of a wound filler that comprises a bubble wrap material. The material may include a layer having a plurality of variable sizes bubbles spread across a surface of the layer. As illustrated in FIG. 10B, the layer may be wrapped or roller into a spiral or other configuration when placed in the wound. FIG. 10B illustrates a top view of a wound showing how the bubble wrap would be placed in the wound in one embodiment, though the bubble wrap may be placed in the wound in any suitable configuration. When the wound filler is used in a negative pressure system as described above, the variable size bubbles will collapse under varying pressures in the wound.

FIGS. 11A-11C illustrate another embodiment of a wound filler comprising a bubble wrap material. In this embodiment, layers of bubble wrap material may be provided one on top of the other in the wound. For example, as shown in FIG. 11B, adjacent layers may be provided where the bubbles face each other. As shown in FIG. 11C, when used in a negative pressure system as described above and when under negative pressure, the bubbles may preferentially collapse in one direction (e.g., a horizontal direction) but remain vertically rigid.

In some embodiments, it may be desired to control the closure of a wound by controlling the volume, stiffness, pressure, and/or collapse of any of the wound fillers described herein this section or elsewhere in the specification. In some embodiments, the closure can be controlled based on measurement of internal pressure within the wound, for example by monitoring at least one of a bladder pressure, an aortic pressure, a pressure within the colon, a pressure within the uterus, a limb pressure, and a blood flow rate. For example, as will be described in greater detail below, feedback from the internal pressure mechanism can be used to manually or automatically control the rate of collapse or the compression of the wound filler, thereby controlling the rate of closure of a wound. Further details regarding these and other embodiments are described below and in U.S. Provisional Application No. 61/782,026, filed Mar. 14, 2013, entitled APPARATUSES AND METHODS FOR WOUND THERAPY, the entirety of which is hereby incorporated by reference.

Figure 12:
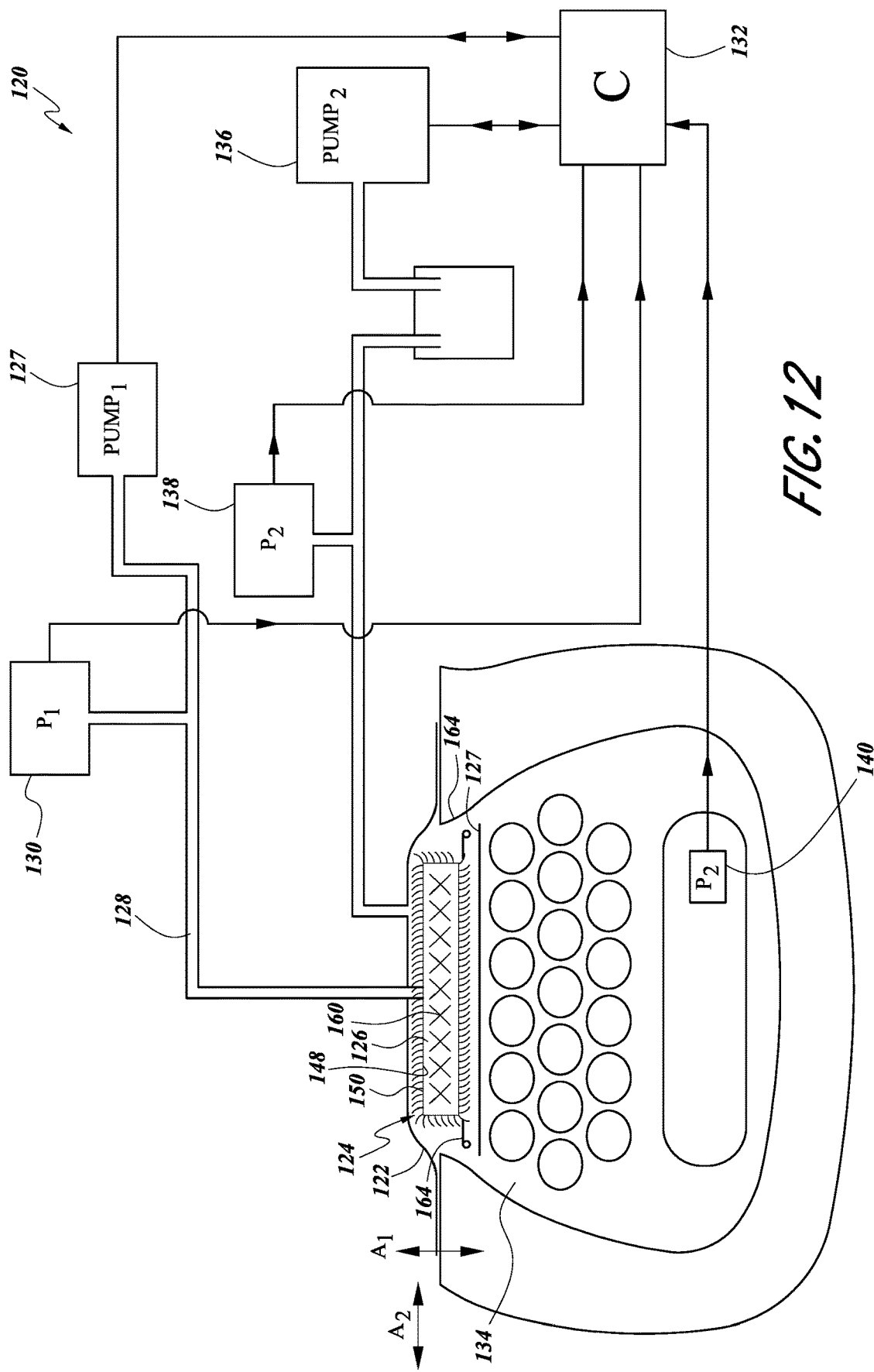
FIG. 12 is a schematic representation of an embodiment of an apparatus used to provide negative pressure wound therapy to a wound.
Figure 13:
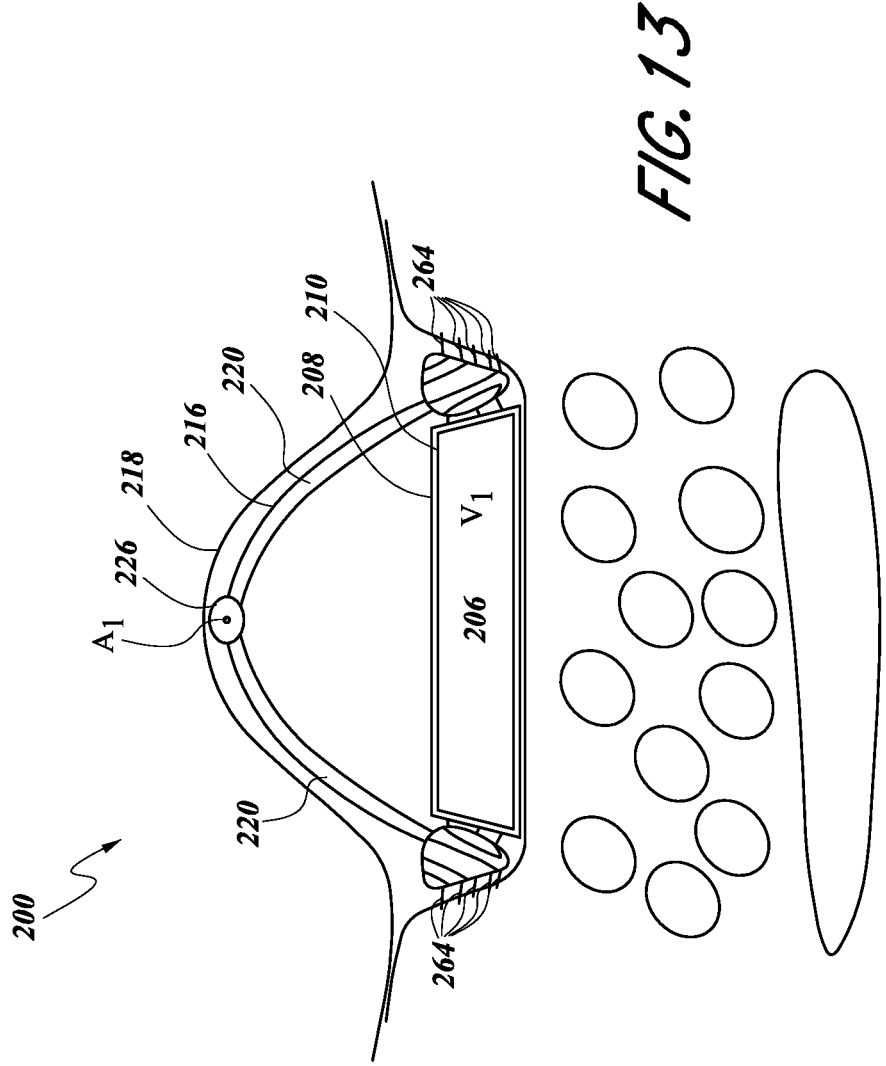
FIG. 13 is a schematic representation of another embodiment of an apparatus used to provide negative pressure wound therapy to a wound, showing the wound in first state of contraction.
Figure 14:
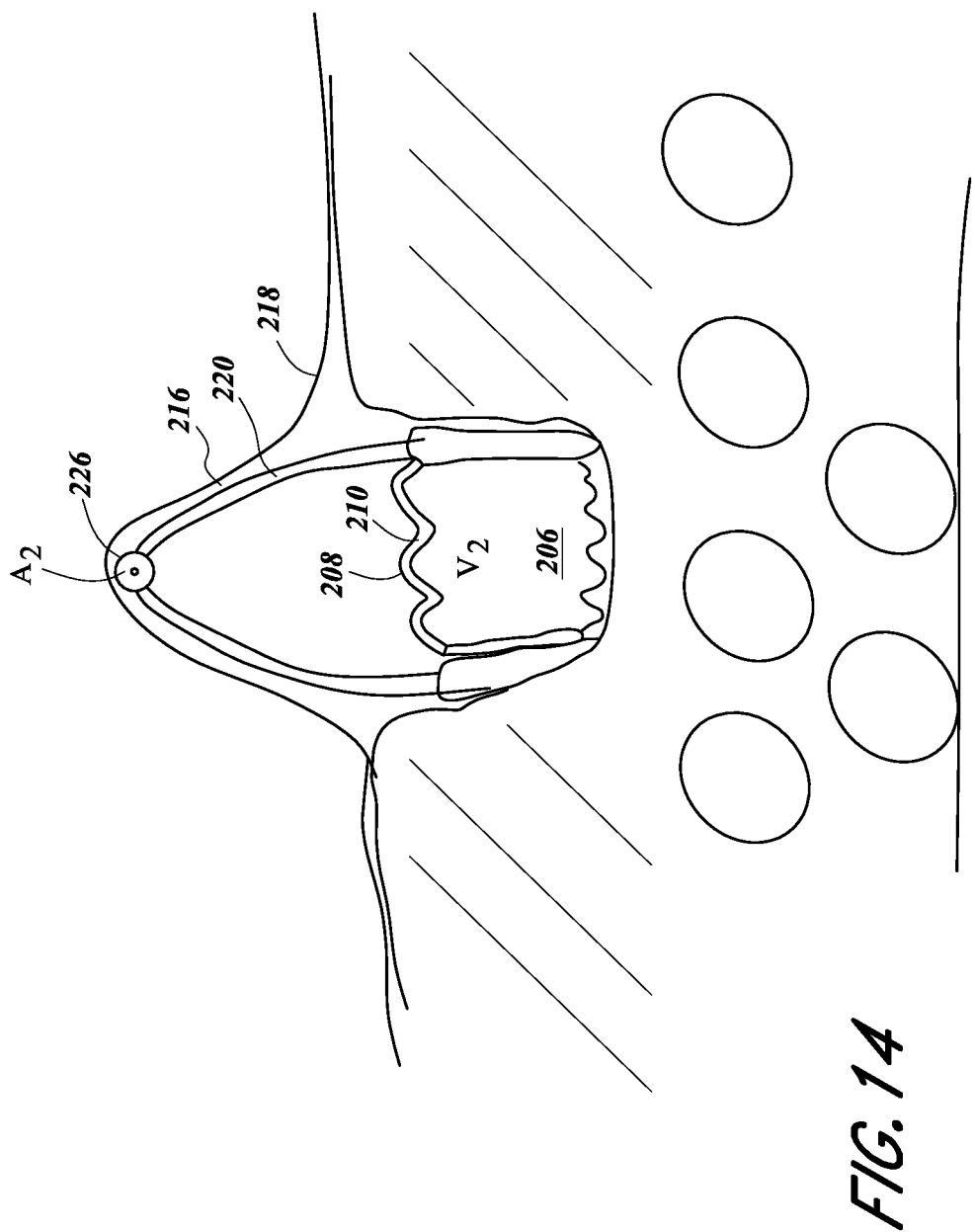
FIG. 14 is a schematic representation of another embodiment of an apparatus used to provide negative pressure wound therapy to a wound, showing the wound in second state of contraction.

The Apparatuses and Methods of FIGS. 12-14

Compartment syndrome can occur when excessive pressure builds up inside an enclosed space in the body. Excessive pressures in the abdominal compartment, for example, can impede the flow of blood to and from the affected tissues, bodily organs, or even the lower extremities if excessive pressure is exerted on the abdominal aorta. The pressure buildup within the abdominal compartment can be the result of excessive fluid buildup in the abdominal compartment, in addition to or alternatively as a result of the forces exerted on the abdominal region from the application of negative pressure wound therapy to the abdominal compartment.

Such excessive pressure can cause permanent injury or damage to the tissues, organs (such as the liver, bowels, kidneys, and other organs), and other body parts affected by the reduction of blood flow. Therefore, preventing the buildup of excessive pressures in the abdominal compartment is beneficial for the treatment of abdominal injuries.

Internal abdominal pressure may also be measured and/or monitored indirectly using intragastric, intracolonic, intravesical (bladder), inferior vena cava catheters, or by other suitable methods, such as via the uterus. In some arrangements, for example, the internal pressure may be measured by inserting a catheter into the patient's bladder. Aortic blood pressure can also be monitored using techniques known in the field. For limb-based compartment syndrome, the internal pressure can be measured by a needle inserted into the affected limb, and preferably, the pressure measured there should be within 20-30 mmHg of the patient's diastolic blood pressure. The clinician can also monitor for a pulse distal of the affected extremity.

In addition to any of the foregoing methods or devices for measuring internal pressure, or any combination of such, in some embodiments, negative pressure wound therapy can be applied to the wound of a patient in a manner to minimize or prevent the build-up of excessive pressure that causes compartment syndrome. For example, any of the negative pressure wound therapy dressing components and/or fillers disclosed herein can be configured to support or contain one or more pressure sensors configured to permit a clinician to monitor the internal pressure within the compartment, wound cavity, or abdominal cavity. In some embodiments, the negative pressure dressing components may include a wound filler that may have an adjustable volume, such as an inflatable bladder or other wound fillers as described below, which when placed within a wound can control how much the wound can close. In one example, one or more pressure sensors can be added to the dressing components, including without limitation positioning one or more pressure sensors on the surface of and/or inside any inflatable bladder embodiment disclosed herein (such as described below with respect to FIG. 12) that can be positioned in the abdominal cavity. The pressure sensors can be supported on, embedded within, or be integral with an outer and/or inner surface of any inflatable bladder embodiments disclosed herein, and can be used to monitor the pressure exerted on the inflatable bladder from the adjacent tissues and organs within the abdominal cavity to alert the patient or caregiver when a threshold or potentially harmful pressure is present within the abdominal cavity.

Additionally or alternatively, one or more pressure sensors can be positioned on or supported by a portion of any wound packing or wound filler components positioned within or adjacent to the wound cavity, or embedded within a portion of the wound filler and/or the dressing overlay or cover, including being supported by the overlay itself, and/or any conduit components of the dressing. The pressure sensors can therefore be positioned on, supported by, or embedded within any combination of the dressing components disclosed herein.

Furthermore, in addition or alternatively to any of the sensor positions located herein, one or more pressure sensors can also be positioned adjacent to one or more of the organs in the cavity being treated, for example the bladder, one or more kidneys, and/or any other organs or proximally located tissue surfaces.

Some embodiments can have one or more pressure sensors supported by or on or embedded within the wound packing layer or wound filler, one or more pressure sensors supported by or on or embedded within one or more of the organs (such as the bladder) or tissue layers in the cavity, and one or more pressure sensors supported by or on or embedded within one or more inflatable bladders positioned within the wound cavity.

Monitoring the pressure in one, some or all of these three locations can permit the caregiver to optimize or control the level of negative pressure applied to the wound cavity, optimize or control a level of inflation or pressure of an inflatable bladder placed within the wound, optimize or control the collapse, stiffness or volume of a wound filler placed within the wound, and/or monitor a level of pressure exerted on one or more organs, tissue layers, blood vessels, or other body parts affected by the closure pressures. A caregiver can then adjust a level of pressure in the inflatable bladder by either adding fluid to the bladder or releasing fluid from within the bladder to a receptacle or container positioned outside the body, adjust the collapse, stiffness or volume of the wound filler, adjust a level of negative pressure exerted on the wound cavity, and/or adjust any other closure forces applied to the wound to either increase or decrease the closure forces. In some embodiments, these adjustments can be made dynamically or automatically by a computer controller that receives one or more pressure readings or other data indicative of excessive pressure, and that sends a control signal to a pump or other device to make the adjustments.

In certain embodiments, when the computer controller receives a signal from a sensor, such as any sensor disclosed herein this section or elsewhere in the specification, the controller may trigger an alarm. Such an alarm may be an audible and/or visual alarm to alert a caregiver to a particular reading. However, any suitable alarm may be used. In some embodiments, the alarm may trigger when a pressure reading has crossed above or below a particular threshold, such as when the pressure on an organ is too high. In certain embodiments, the alarm may trigger when the level of negative pressure rises above or falls below a certain threshold. As will be appreciated by one of skill in the art, since there are many possible sensor configurations disclosed within this specification, there may also be any number of suitable corresponding alarms.

A clinician may monitor the internal pressure as vacuum is slowly increased to the wound dressing, or as air is slowly released from the inflatable member. In one embodiment, human bladder pressure is controlled below approximately 40 mmHg, or below approximately 30 mmHg, approximately 20 mmHg, or approximately 15 mmHg. In some embodiments, the measurement of internal pressure and control of the vacuum and air release can be controlled automatically. This way, as the oedema decreases the wound can be slowly closed further over, for example, a period of hours to days (e.g., closure by seven days). It will be appreciated that systems can be employed where the vacuum can be slowly applied with pressure feedback being provided based on vital signs of the patient or other monitoring described herein or in http://www.uptodate.com/contents/abdominal-compartment-syndrome.

FIG. 12 is a schematic representation of an apparatus 120 used to provide negative pressure wound therapy to a wound and to control the level of therapy and/or closure of the wound based on pressure sensors positioned within the wound cavity to minimize the risk of compartment syndrome. For example and without limitation, in some embodiments, the apparatus 120 can have a backing layer 122 for providing a substantially air and liquid-tight seal over a wound. Under the overlay, the apparatus 120 can have a wound packing member or wound filler 124 that can have an adjustable volume and/or internal pressure. For example, some embodiments of the wound packing member 124 can have a sealed member 126 (such as a sealed bag) that can be controllably inflatable and deflatable from a pressure source such as a pump via a conduit 128 in communication with a sealed space within the sealed member 126. The sealed member 126 can be positioned in the wound in contact with the wound tissue interface. For example, in any embodiments used for abdominal wounds, the sealed member 126 can be configured and can be positioned in the wound cavity so as to engage all tissue layers above the organs in the body. For example, in some embodiments, the sealed member 126 can be positioned in the wound so as to contact any or all of the layers that can be present in an abdominal wound, such as (from deepest to most superficial) the peritoneum, extraperitoneal fascia (deep fascia), muscle, superficial fascia, subcutaneous tissue, and skin. However, the presence or absence of various layers is location dependent, so not all of these layers may be present in every abdominal wound treatable with the apparatuses of the present disclosure.

In some embodiments, an organ protection layer 127, such as any embodiments of the wound contact layer disclosed in U.S. Application Publication No. 2011/0213287, Ser. No. 12/886,088, titled SYSTEMS AND METHODS FOR USING NEGATIVE PRESSURE WOUND THERAPY TO MANAGE OPEN ABDOMINAL WOUNDS, filed on Sep. 20, 2010, which application is hereby incorporated by reference herein as if fully set forth herein, can be positioned between the sealed member 126 and the viscera or other organs. Embodiments of the apparatus 120 disclosed herein can comprise any of the other components, materials, features, or details of any of the embodiments or components of the negative pressure systems disclosed in U.S. application Ser. No. 12/886,088. As mentioned, all embodiments or components of the negative pressure systems disclosed in U.S. application Ser. No. 12/886,088 are hereby incorporated by reference as if fully set forth herein.

A pressure sensor 130 (also referred to herein as a first pressure sensor) can be used to monitor a pressure level within the sealed member 126. The pressure sensor 130 can provide a visual reading of the level of pressure within the sealed member 126, and/or can provide a signal to a controller 132 based on the level of pressure within the sealed member.

The level of pressure within the sealed member 126, as mentioned, can be controlled in part by the pump 127 (also referred to herein as the first pump) and can be adjusted to be a positive or a negative pressure. Additionally, in some embodiments, the pump 127 can be configured to cycle the pressure level between any desired positive or negative pressure levels or to apply intermittent pressure to the sealed member 126. Positive pressures within some embodiments of the sealed member 126 or any sealed member embodiment disclosed herein can range from 0 mmHg to 60 mmHg or more. Negative pressures within some embodiments of the sealed member 126 or any sealed member embodiment disclosed herein can range from 0 mmHg to −180 mmHg or more.

In any embodiments disclosed herein, the pressure level within the sealed member 126 can be controlled independently of the pressure in a space 134 beneath the backing layer 122. The pressure beneath the backing layer 122 can be detected by a pressure sensor (such as pressure sensor 138, which is also referred to herein as a second pressure sensor) in communication with the space 134 beneath the backing layer 122. The second pressure sensor 138 can be configured to provide a signal to the controller 132. In any embodiments disclosed herein, a second pump, such as pump 136, can be used to provide a source of negative pressure to a space 134 beneath the backing layer 122. Alternatively, the apparatus can be configured to have only one pump (not illustrated) having multiple conduits and multiple valves to independently control a level of pressure within the sealed member 126 and the space 134 beneath the backing layer 122.

In some embodiments, the level of pressure within the sealed member 126 can be adjusted independent of the level of reduced pressure in the space 134 to increase or decrease a volume of the sealed member 126, which can be beneficial in terms of controlling a level of pressure exerted on one or more organs in the abdominal area and, hence, can be beneficial in terms of controlling or minimizing a risk of compartment syndrome. A pressure sensor 140 (which is also referred to herein as a third pressure sensor) can be placed in communication with a human organ, for example the human bladder to monitor pressure within the human bladder. The third pressure sensor 140 can also be configured to provide a signal to the controller based on the pressure reading detected by the third pressure sensor 140.

If a pressure detected in one or more organs, such as the human bladder, as detected by a pressure sensor 140, exceeds a threshold value, the controller 132 can adjust one or more pressure levels to reduce the pressure exerted on the organ or organs. In some embodiments, the threshold value of pressure measurements for organs in the abdominal region can be 10 mmHg (or approximately 10 mmHg), or 12 mmHg (or about approximately 12 mmHg), or 15 mmHg (or about 15 mmHg) but such values may be organ specific and/or patient specific. Additionally, in some applications, wherein any of the dressings disclosed herein are used to treat a wound on the thigh, for example, compartment pressures can reach as high as 120 mmHg, such that the threshold value of compartment pressure in that region may be much higher than for abdominal wounds, such as approximately 60 mmHg or less to approximately 80 mmHg, or approximately 100 mmHg. In the leg, generally, the threshold value of pressure which can trigger such pressure and dressing adjustments can be approximately 40 mmHg, or from approximately 40 mmHg to approximately 60 mmHg. Some embodiments of the apparatus can configured such that a medical practitioner can set the level of the threshold value, since a different value may be applicable to each patient. For younger patients or children, or patients that are at a higher risk for developing compartment syndrome, for example, a lower threshold value can be set. In some embodiments, the threshold value can be set at from approximately 8 mmHg to approximately 12 mmHg.

For example, in abdominal negative pressure wound therapy kits, to reduce the pressure buildup, the apparatus can be configured to decrease the level of closure forces applied to the wound. This can be achieved in some embodiments by increasing a level of pressure in the sealed member 126, thereby limiting the amount of closure in the walls of the wound interface even when an elevated level of reduced pressure applied to the space 134 in the wound is maintained to ensure an appropriate level of fluid removal. This can be done until the level of pressure in one or more of the organs, such as the bladder, or blood flow rate measurements, reach a safe or below-threshold value once again. In some embodiments, the pressure level within the sealed member 126 can be a positive value (i.e., above atmospheric) to exert a spreading force on the tissue interface, while the pressure level within the space 134 but outside of the sealed member 126 is at a negative pressure level. This arrangement wherein the sealed member 126 can independently control the level of closure of the wound interface, can also permit a medical practitioner to exceed the normal negative pressure levels in the space 134 beyond the typical therapeutic ranges that might otherwise have been limited by excessive interabdominal pressure levels.

In some embodiments or arrangements, a sealed member 126 can be sized and configured to contact the peritoneum, extraperitoneal fascia (deep fascia), muscle, superficial fascia, subcutaneous tissue, and skin when placed in the abdominal wound. When the level of closure of the wound interface is desired to be limited, such as when excessive levels of pressure are present in or adjacent to the wound area, a level of pressure within the sealed member 126 can be increased to limit the contraction in one or more of the peritoneum, extraperitoneal fascia (deep fascia), muscle, superficial fascia, subcutaneous tissue, and skin, thereby increasing the volume of space that the viscera can occupy and reducing the level of pressure exerted on the various organs and blood vessels. Again, because the level of pressure within the sealed member 126 can be adjusted independently of the level of pressure within the space 134 beneath the backing layer 122 but outside of the sealed member 126, a therapeutic level of reduced pressure can be applied to the wound to remove excessive liquid exuded in the abdominal compartment and improve the healing conditions.

In any of embodiments disclosed herein, the apparatus can gather pressure readings from one or more pressure sensors positioned throughout the body to monitor compartment pressures. For interabdominal compartment pressures, readings can be gathered in the abdominal region or adjacent thereto. For example, any apparatus disclosed herein can have one or more blood flow meters (such as a laser Doppler blood flow meter) configured to measure a flow rate of blood through target blood vessels, arteries, capillaries, and/or muscles. Any embodiments of the laser Doppler can be permanently mounted to the patient's skin near the wound cavity. In some embodiments, for example, one or more blood flow meters can be used to measure a flow rate of blood through the femoral arteries or through musculature at or near to the abdominal region and provide a feedback signal to the controller 132.

Additionally, in some embodiments, pressure levels in, for example, the abdominal compartment can be measured using the vesicular technique, which can involve the use of an indwelling urinary catheter, a pressure transducer, and a syringe or similar device capable of infusing fluid. Additionally, pressure levels in the abdominal compartment can be measured by catheterizing the inferior vena cava through either the left or right femoral artery. See F. Lui, A. Sangosanya, and L. J. Kaplan, "Abdominal Compartment Syndrome: Clinical Aspects and Monitoring," *Critical Care Clinics*, vol. 23, no. 3, pp. 415-433, 2007 for more information about monitoring techniques for suitable for monitoring abdominal compartment syndrome.

Further, any embodiments of the sealed member 126 disclosed herein can be formed from a substantially sealed impermeable membrane 148, that seals around or to the conduit 128 that provides the fluid (e.g., air, nitrogen, or argon, or saline, water, or other liquids) into and out of the impermeable membrane 148, which can be formed from any suitable, biocompatible polymer film, sheet, bag, pouch, chamber, or otherwise, similar to any of the inflatable membranes disclosed in U.S. Pat. No. 7,753,894, which is application Ser. No. 12/886,088, titled WOUND CLEANSING APPARATUS WITH STRESS, filed on Dec. 17, 2007.

In some embodiments, the sealed member 126 can have a foam layer 150 around some or all of the outside surface of the impermeable membrane 148. In some embodiments, the foam layer 150 can surround the entire surface of the impermeable membrane 148. The foam 150 can help cushion any pressure points exerted on the tissue by the sealed member 126, and can assist with the distribution of negative pressure across the wound cavity.

Additionally, though not required, any embodiments disclosed herein can have a structural member 160 positioned inside the impermeable membrane 148. In some embodiments, the structural member 160 can be configured to be more rigid in a vertical direction (i.e., transverse to the backing layer, as indicated by arrow A1 in FIG. 12), than in a lateral direction (i.e., in the direction of wound closure of the tissue interfaces, as indicated by arrow A2 in FIG. 12). Examples of structural members that can be used are found in application Ser. No. 13/365,615, titled "Negative Pressure Wound Closure Device," filed Feb. 3, 2012, published as US 2012/0209227, the entirety of which is hereby incorporated by reference.

In some embodiments, the sealed member 126 can have multiple, independently controllable (e.g., inflatable or deflatable) chambers. One or more manifolds can control the inflation and deflation of the various compartments or chambers to control the size and/or shape of the bladder member as desired to suit the particular wound size and application.

Additionally, in any embodiments disclosed herein, the sealed member 126 can be used with a vertically rigid but laterally collapsible structure positioned either inside or outside of the sealed member 126. For example, with reference to FIG. 13, another embodiment of an apparatus 200 is illustrated. The apparatus 200 can have any of the same features, components, or details of any other embodiments disclosed herein, including any of the visualization elements and the pressure sensors disclosed above. Additionally, as shown in FIG. 13, a sealed member 206 can be positioned in the wound cavity and have any of the same features, materials, or other details of the sealed member 126 disclosed herein, including but not limited to the foam layer or interface 208 surrounding the impermeable layer 210.

The apparatus 200 can also have a support member 216 positioned under a backing layer 218. Some embodiments of the support member 216 can have one or more legs (also referred to herein as a body portion) 220 attached to a top portion 226 (also referred to herein as a first portion) of the support member 216. In some embodiments, the top portion 226 of the support member 216 can be along an apex of the support member 216 and define a longitudinal axis A1 of the support structure. The legs 220 can be rotatably supported by the top portion 226 so that the legs 220 can rotate about axis A1 defined through the axial centerline of the top portion 226. The sealed member 206 can be coupled with, connected to, adhered to, or otherwise attached the legs 220 such that contracting or expanding the sealed member 206 will correspondingly contract or expand the legs 22 and support member 216. In some embodiments, the legs 220 can be positioned within molded pockets formed in the sealed member 206. In some embodiments, one or more foam pockets positioned at the bottom of the legs 220 can be adhered to the sealed member 206.

In this configuration, as the sealed member 206 is contracted from a first volume, such as volume V1 shown in FIG. 13, to a second, larger volume, such as volume V2 shown in FIG. 14, the support member 216 (or any other suitable support member having greater vertical than lateral rigidity) can also laterally contract. Additionally, the sealed member 206 can be configured to expand from a smaller volume, such as volume V2 shown in FIG. 14, to a larger volume, such as volume V1 shown in FIG. 13, the so as to urge the support member 216 and the legs 220 thereof, laterally outward against the walls of the wound interface, thereby potentially reducing the pressure on the organs within the abdominal compartment. As the wound closes during the course of healing, the legs 220 can rotate closer together so that the closure of the wound is not inhibited by the dressing backing layer 218.

Further, some embodiments of the wound closure apparatuses, such as embodiments 120 and 200, can have one or more tissue engaging elements supported by the sealed member or the support member in communication with the sealed member. The tissue engaging elements can be configured to engage one or more layers of the wound interface, including any one or combination of the peritoneum, extraperitoneal fascia (deep fascia), muscle, superficial fascia, subcutaneous tissue, and skin. The tissue engaging elements 164 (schematically represented in FIG. 12) of the embodiment of the apparatus 120 shown in FIG. 12, or the tissue engaging elements 264 of the embodiment of the apparatus 200 can comprise any one or combination of tissue connectors, tissue anchors, hook shaped members, balls on the ends of rods, and/or any other suitable engaging mechanisms available for use with the various layers of tissue. Some embodiments of the sealed member 126 can have any combination of different tissue engaging elements desired to engage the various different tissue layers in the wound site.

In any embodiments of the sealed member disclosed herein, a level of the volume of fluid within the sealed member can be controlled automatically by the control system, as discussed. Additionally, in any embodiments, the level of the volume of fluid within the sealed member can be changed manually by adding or removing fluid into the sealed member through a tube and a hand operated pump system, or through a syringe and cannula device inserted into a sealed receptacle such as one or more syringe ports on the sealed member, in response to pressure readings acquired by any of the plurality of pressure sensors in the apparatus.

In some embodiments, the sealed member can itself be more rigid in a vertical direction than in a lateral direction. For example, any embodiments of the sealed member can have corrugations or an undulating surface that causes the sealed member to be more flexible in a lateral direction than in a vertical direction. In some embodiments, the sealed member can have, for example, an accordion-like shape.

It will be appreciated that in some embodiments, it is not necessary to take any measurements indicative of excessive pressure within the patient. Rather, it may simply be desired to control the closure of a wound by controlling the volume, stiffness, pressure, and/or collapse of any of the wound fillers described above. Such closure can be controlled based on visual inspection, use of the wound visualization methods and apparatus described above, or can be controlled based on a desired predetermined schedule. The control over such closure can be performed manually by a health practitioner, or may be performed automatically or based on inputs by a controller as described above. For example, where an inflatable bladder is placed in the wound, the pressure in the bladder may be manually or automatically controlled to limit and/or allow a certain amount of wound closure for a given period of time. This concept may similarly be applied to wound fillers such as described in FIG. 13 by including a mechanism (such as the adjustable bladder between the legs) where the angle between the legs can be controlled over time. Other embodiments of wound fillers whose volume, stiffness, pressure and/or collapse may be controlled, can be used with any of the components of any of the embodiments disclosed herein. Examples of such additional wound fillers that can be used with any of the components of any of the embodiments disclosed herein are found in application Ser. No. 13/365,615, titled "Negative Pressure Wound Closure Device," filed Feb. 3, 2012, published as US 2012/0209227, incorporated by reference herein, the entirety of which is hereby incorporated by reference and should be considered a part of this specification. It will be appreciated that any of these embodiments of wound fillers may also be used in combination with or instead of the inflatable bladder in the system and method of FIG. 12.

In other embodiments, such closure can be controlled based on visual inspection, the use of the wound visualization methods and apparatus as described herein this section or elsewhere in the specification, or based on a desired predetermined schedule. The control over such closure can be performed manually by a health practitioner, or may be performed automatically or based on inputs by a controller as described herein this section or elsewhere in the specification. For example, where an inflatable member such as described herein this section or elsewhere in the specification is placed in the wound, the pressure in the inflatable member may be manually or automatically controlled to limit and/or allow a certain amount of wound closure for a given period of time. This concept may similarly be applied to other wound fillers described herein this section or elsewhere in the specification, for example as described in FIG. 13, by including a mechanism (such as the adjustable bladder between the legs) where the angle between the legs can be controlled over time. Other mechanisms can also be employed to control the change in volume, stiffness, pressure, and/or collapse of any of the wound fillers described herein, either manually by a user or automatically based on control for a controller. It will further be appreciated that any of the embodiments of wound fillers as described above may also be used in combination with or instead of the inflatable bladder in the system and method of FIG. 12.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A wound treatment apparatus for use with negative pressure, comprising:
   a wound filler for use in treating a wound with negative pressure, comprising:
      a layer comprising a plurality of enclosed dome-shaped bubbles spread across a surface of the layer; and
      wherein the bubbles are configured to collapse under negative pressure.

2. The wound treatment apparatus of claim 1, wherein the plurality of enclosed dome-shaped bubbles are variable-sized bubbles.

3. The wound treatment apparatus of claim 1, wherein the plurality of enclosed dome-shaped bubbles are configured to collapse in one direction.

4. The wound treatment apparatus of claim 1, wherein the plurality of enclosed dome-shaped bubbles are configured to collapse in a horizontal direction while remaining rigid in a vertical direction.

5. The wound treatment apparatus of claim 1, wherein the layer comprising a plurality of enclosed dome-shaped bubbles spread across a surface of the layer is a first layer, and wherein the wound filler further comprises a second layer comprising a plurality of bubbles spread across a surface of the second layer.

6. The wound treatment apparatus of claim 5, wherein the first layer and the second layer are layered one on top of the other.

7. The wound treatment apparatus of claim 5, wherein the first layer and the second layer are layered one on top of the other such that the plurality of enclosed dome-shaped bubbles on the first layer face the plurality of bubbles on the second layer.

8. The wound treatment apparatus of claim 1, wherein the layer comprises a plurality of openings.

9. A wound treatment apparatus for use with negative pressure, comprising:
   a wound filler for use in treating a wound with negative pressure, comprising:
      a layer comprising an array of enclosed bubbles spread across a surface of the layer, wherein the bubbles are spaced apart from each other by gaps both along a length and a width of the layer; and
      wherein the array of enclosed bubbles are configured to collapse under negative pressure.

* * * * *